US007635558B2

(12) United States Patent
Madjar et al.

(10) Patent No.: US 7,635,558 B2
(45) Date of Patent: Dec. 22, 2009

(54) METHOD FOR ANALYZING NUCLEIC ACID AND USE THEREOF FOR EVALUATING THE DEGREE OF MRNA EDITING OF THE SEROTONIN 5-HT$_{2C}$ RECEPTOR

(75) Inventors: Jean-Jacques Madjar, Lyons (FR); Hervé Berthomme, Bron (FR)

(73) Assignee: Biocortech, Paris (FR)

( * ) Notice: Subject to any disclaimer, the term of this patent is extended or adjusted under 35 U.S.C. 154(b) by 498 days.

(21) Appl. No.: 10/522,592

(22) PCT Filed: Jul. 24, 2003

(86) PCT No.: PCT/FR03/02339

§ 371 (c)(1),
(2), (4) Date: Jan. 25, 2005

(87) PCT Pub. No.: WO2004/011594

PCT Pub. Date: Feb. 5, 2004

(65) Prior Publication Data

US 2008/0075662 A1 Mar. 27, 2008

(30) Foreign Application Priority Data

Jul. 26, 2002 (FR) .................................. 02 09524

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)
*B01D 57/02* (2006.01)

(52) U.S. Cl. .................. 435/6; 435/91.2; 536/23.1; 536/24.3; 536/25.3; 204/451

(58) Field of Classification Search .................. 435/6, 435/91.2; 536/23.1, 24.3, 25.3; 204/451
See application file for complete search history.

(56) References Cited

U.S. PATENT DOCUMENTS 5,487,972 A * 1/1996 Gelfand et al. .................. 435/6
5,578,467 A 11/1996 Schuster et al.
6,156,501 A * 12/2000 McGall et al. .................. 506/9
2001/0034023 A1* 10/2001 Stanton et al. .................. 435/6

FOREIGN PATENT DOCUMENTS

EP 0 552 931 A1 7/1993
WO WO 02 38809 A1 5/2002

OTHER PUBLICATIONS

Larsen et al, High throughput single strand conformation polymorphism analysis, 1999, Huamn mutation, 13, 318-327.*
International Search Report in Corresponding PCT application No. PCT/FR03/02339.

Niswender et al., Identification and characterization of RNA editing events within the 5-HT$_{2C}$ receptor, *Annals of the New York Academy of Sciences*, vol. 861, pp. 38-48 (1998).
Nguyen et al., Studies towards the design of a modified GC base pair with stability similar to that of the AT base pair, *Tetrahedron Letters*, vol. 38, No. 23, pp. 4083-4087 (1997).
Niswender, Coleen, Strategies and requirements for the detection of RNA editing in G protein coupled-receptor RNA, *Methods in Enzymology*, vol. 343, pp. 476-492 (2002).
Zhong et al., Detection of apolipoprotein B mRNA editing by peptide nucleic acid mediated PCR clamping, *Biochemical and Biophysical Research Communications*, vol. 259, pp. 311-313 (1999).
Fuchs et al., RNA editing in higher plant plastids: oligoribonucleotide SSCP analysis allows the proof of base conversion directly at the RNA level, *Current Genetics*, vol. 39, No. 5-6, pp. 384-387 (Jul. 2001).
Ibrahim, et al., Differential expression of potato U1A spliceosomal protein genes: a rapid method for expression profiling of multigene families, *Plant Molecular Biology*, vol. 45, No. 4, pp. 449-460 (Mar. 2001).
Maekawa, et al., Relative ratios of mRNA molecules encoded by genes with homologous sequences using fluorescence-based single-strand conformation polymorphism analysis; *Biochemical and Biophysical Research Communications*, vol. 223, No. 1, pp. 520-525 (1996).
Ellison, Jane, Fluorescence-based mutation detection, *Molecular Biotechnology*, vol. 5, No. 1, pp. 17-31 (1996).

* cited by examiner

*Primary Examiner*—JD Schultz
*Assistant Examiner*—Narayan K Bhat
(74) *Attorney, Agent, or Firm*—Finnegan, Henderson, Farabow, Garrett & Dunner, L.L.P.

(57) ABSTRACT

The invention concerns a method for analyzing nucleic acids using a small-size probe array comprising deoxyinostines (dI) instead of deoxyguanogines (dG). The invention also concerns such probe arrays and their use in methods for detecting and/or quantifying target oilgonucleotides present in DNA (deoxyribonucleic acid) or RNA (ribonucleic acid) molecules in a sample, in particular mRNA editing rate of the serotonin 5-HT$_{2C}$ receptor (5-HT$_{2C}$-R). The invention further concerns a biochip or a reactor in liquid medium comprising such probe arrays as well as their uses, in particular for detecting and/or identifying genetic polymorphisms or for determining an mRNA editing rate, whether it is that of a 5-HT$_{2C}$-R mRNA or any other RNA capable of being edited. The invention also concerns a method based on the isolation of a single strand conformation polymorphism (SSCP) enabling under specific analysis conditions the editing profile and/or rate of an mRNA capable of being edited to be obtained, as well as a method for diagnosing diseases or susceptibility to diseases associated with the degree of edition of an mRNA. Finally, the invention concerns a method for selecting compounds capable of modulating mRNA editing rate, in particular that of 5-HT$_{2C}$-R, as well as the use of such compounds for preparing a pharmaceutical composition for treating organic fluid.

3 Claims, 1 Drawing Sheet

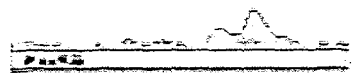 Rat choroid plexus  FIGURE 1A
 Rat total brain  FIGURE 1B
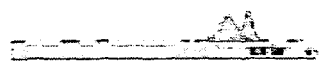 D  FIGURE 1C
 ABC'  FIGURE 1D
 Non edited  FIGURE 1E
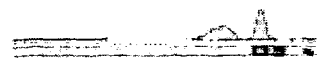 AD  FIGURE 1F
 AB  FIGURE 1G
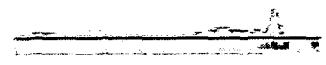 A  FIGURE 1H
 ABC  FIGURE 1I
 ADC'  FIGURE 1J
 CD  FIGURE 1K
 ACD  FIGURE 1L
 CC'  FIGURE 1M
 ABCD  FIGURE 1N
 ABD  FIGURE 1O

METHOD FOR ANALYZING NUCLEIC ACID AND USE THEREOF FOR EVALUATING THE DEGREE OF MRNA EDITING OF THE SEROTONIN 5-HT$_{2C}$ RECEPTOR

The present invention relates to a method for analyzing nucleic acids using a small-size probe array comprising deoxyinosines (dI) instead of deoxyguanosines (dG). The invention also comprises such probe arrays and their use in methods for detecting and/or quantifying target oligonucleotides present in DNA (deoxyribonucleic acid) or RNA (ribonucleic acid) molecules in a sample, in particular the determination of the editing rate for the serotonin 5-HT$_{2C}$ receptor (5-HT$_{2C}$-R) messenger RNA (mRNA). The invention also relates to a biochip or to a reactor in liquid medium comprising such probe arrays and also to the uses thereof, in particular for detecting and/or identifying genetic polymorphisms or for determining an mRNA editing rate, whether it is that of. the 5-HT$_{2C}$-R mRNA or of any other RNA capable of being edited. A subject of the present invention is also a method based on the demonstration of a single strand conformation polymorphism (SSCP) making it possible, under given analytical conditions, to obtain the editing profile and/or rate of an mRNA capable of being edited, and a method for diagnosing diseases or susceptibility to diseases associated with the degree of editing of an mRNA. A subject of the present invention is also a method for selecting compounds capable of modulating mRNA editing rate, in particular that of 5-HT$_{2C}$-R, and also the use of such compounds for preparing a pharmaceutical composition intended for treating mood.

Among the methods for analyzing nucleic acids which make it possible to detect a difference of one or of a few nucleotides in a given sequence, two major categories of methods can be distinguished, those which are specific for a single sequence and those which make it possible to simultaneously detect, by hybridization in the form of a double-stranded DNA duplex or in the form of a DNA/RNA heteroduplex, several different sequences (up to several thousand).

In the first category may be placed—without being limiting since there are so many variants and without describing them since they have all been widely used to varying degrees— DNA sequencing, direct sequencing or sequencing after iterative amplification by PCR (polymerase chain reaction), possibly preceded by a reverse transcription reaction (RT-PCR for reverse transcription followed by PCR); the demonstration of a restriction fragment length polymorphism (RFLP) subsequent to one or more point mutations which affect one or more restriction sites, and its variant, AFLP (amplified fragment length polymorphism); ligase chain reaction (LCR) and its variant, ligase detection reaction (LDR); PCR-mutant allele specific amplification (PCR-MASA);

primer extension; etc. For all these methods and those which are derived therefrom, see "Current Protocols in Molecular Biology", John Wiley & Sons publishers, 4 vol. updated per trimester, ISBN 0-471-50338-X.

In the second category, are the methods of analysis by hybridization in liquid medium and those derived from the Southern blotting method, which was initially described for DNA (Southern, J. Mol. Biol., 1975, 98:503-517). Among the latter, mention may be made, without any implied limitation, of the Southern method applied to RNA (or Northern blotting, see Alwine et al., Proc. Natl. Acad. Sci. USA, 1977, 74:5350-5354, and Alwine et al., Methods Enzymol., 1979, 68:220-242); hybridizations on a support, macroarray and microarray nucleic acid hybridizations (see Fotin et al., Nucleic Acids Res., 1998, 26(6):1515-1521 and the articles which are referenced therein, see also Diehl et al., Nucleic Acids Res., 2001, 29(7)e38 and the articles which are referenced therein). These hybridizations between nucleic acid molecules which result in the formation of a double-stranded DNA or of a DNA/RNA-type heteroduplex are obtained either in a reactor in liquid medium or, more generally, on a support which may be a hydrophobic membrane (nitrocellulose on Nylon®, for example), or a glass slide that has been activated to allow binding of the single-stranded or double-stranded DNA probes (which, in the latter case, will then be denatured so as to allow hybridization). The deposited DNA sequences which serve as probes for the hybridization of DNA or RNA molecules which are complementary to them may be long, and they are then genomic DNA sequences, generally amplified by PCR, or, more commonly, cDNA (complementary DNA) sequences from mRNA; in the latter case, they come from cDNA libraries of various origins and are in the form of double-stranded DNA. The DNA sequences may also be in the form of single-stranded DNA; in the latter case, they will most commonly be long (60 to 80 bases) or short (approximately 20 bases or less) oligodeoxyribonucleotides. The shorter the oligodeoxyribonucleotides, the more they make it possible to distinguish between sequences which differ, be it by only a single nucleotide. However, this distinction is only possible if the melting temperature Tm of the sequences to be hybridized is very similar or identical.

In fact, while it is possible, by means of the methods of the second category, to demonstrate a sequence difference relating to a single nucleotide, it is necessary, for this to be possible, for the hybridization conditions (salt concentration and temperature essentially) to be sufficiently stringent so that a single base mismatch prevents hybridization between the probe and the target nucleic acid. When these conditions are satisfied, only the probe having the sequence exactly complementary hybridizes with the target nucleic acid, which may be single-stranded DNA or RNA, of desired sequence. For this, the probe must have a sequence that is sufficiently long to allow hybridization that is both stable and specific, but must also be sufficiently short to permit discrimination between nucleic acid (DNA or RNA) populations which exhibit, with respect to one another, a sequence difference of a single nucleotide.

All things being otherwise equal, the temperature at which the specific hybridization is obtained depends essentially on the base composition of the sequences to be paired, adenine, thymine (or uracil), guanine and cytosine, present in the form of deoxyribonucleoside monophosphate in DNA and of ribonucleoside monophosphate in RNA (uracil then replacing thymine), connected to one another by 3'-5'-phosphodiester bonds. The abbreviations dA, dT, dG and dC will be used for deoxyadenosine, deoxythymidine, deoxyguanosine and deoxycytidine monophosphates, respectively, and A, U, G and C will be used for adenosine, uridine, guanosine and cytidine monophosphates, respectively. The richer the sequences are in guanines and cytosines, the higher the temperature which makes it possible to obtain specific hybridization, due to the formation of three hydrogen bonds between these two paired bases, against only two between paired adenines and thymines (or uracils). However, the relative position of these bases within the paired sequences also plays a role in the stability of the DNA double helix or of the DNA/RNA heteroduplex, due to the hydrophobic interactions that certain carbon atoms of the plates of the stacked purine and pyrimidine bases enter into with one another. Consequently, the temperature which makes it possible to obtain specific hybridization and therefore discrimination between two sequences which differ from one another by only a single base depends on the percentage of adenines and thymines (or uracils) and also of guanines and cytosines respectively paired, and also on the relative position of these paired bases in a given sequence.

The temperature which allows specific hybridization can be calculated approximately according to several formulae which take into account the length of the sequences to be paired and also their base composition (see in particular Wallace et al., Nucleic Acids Res. 1979, 6(11):3543-3557 for calculation of the Tm according to the Wallace rule, and also Breslauer et al., Proc. Natl. Acad. Sci. USA, 1986, 83(11): 3746-3750 for calculation of the Tm by the nearest neighbor method). However, no method of calculation makes it possible to precisely determine the Tm of a double-stranded DNA which contains dIs since, in all the formulae currently proposed, the energy for pairing between, firstly, dI and, secondly, dA, dG or dT is considered to be identical, which is incorrect (see below). This temperature can also be determined experimentally by measuring the hyperchromic effect of the DNA as a function of the temperature. For this, the optical density of the double-stranded DNA is measured at 260 nm, continuously, as a function of the temperature. When it is entirely in single-stranded form, DNA absorbs at 260 nm approximately 1.4 times more than when in double-stranded form. The temperature at which DNA is half in double-stranded form and half in single-stranded form is the melting temperature or Tm. The Tm is measured at the point of inflexion of the thermal denaturation curve of the DNA, which represents the value of the optical density measured at 260 nm as a function of the temperature. The greater the number of paired guanines and cytosines in a given sequence, the higher the Tm. It therefore characterizes a double-stranded DNA sequence of given length according to its base composition.

Determining the optimal hybridization temperature in order to ensure discrimination between two sequences which differ only by a single nucleotide and, even more so, by several nucleotides is easy on condition that the sequences to be paired are relatively short.

However, specific hybridization between several probes and as many nucleic acid (DNA or RNA) molecules which differ from one another only by a single nucleotide or which have completely different sequences, with different percentages of adenines and thymines (or uracils) and also of guanines and cytosines respectively paired, requires as many hybridization conditions as there are sequences to be hybridized. In fact, since the conditions which permit specific hybridization depend on the base composition of the sequences to be hybridized, the temperatures required for obtaining specific hybridizations will be higher as the number of paired guanines and cytosines as a replacement for as many paired adenines and thymines (or uracils) increases.

Consequently, it is not possible to obtain, simultaneously on the same solid support, specific hybridizations with small-size set sequences since the temperatures which guarantee the hybridization specificity would have to be different for each sequence to be hybridized, as confirmed by the determination of their Tm.

This impossibility also remains true when it is desired to carry out these specific hybridizations with small-size set sequences in liquid medium in the same reactor, or else in a set of reactors, to which it is desired to apply the same specific hybridization conditions, in particular of temperature, for instance a set of cupules arranged on the same plate or the same microplate.

Thus, it remains desirable to be able to have, today, a method of analysis for carrying out specific hybridizations between nucleic acids of small-size set sequences, sequences differing from one another only by a single nucleotide or sequences that are completely different, permitting hybridizations which result in the formation of duplexes having different percentages of adenines and thymines (or uracils), and also of guanines and cytosines respectively paired, simultaneously on the same solid support, or else in liquid phase in the same reactor or in a set of reactors to which it is desired to apply the same specific hybridization conditions, in particular of temperature.

This is precisely the subject of the present invention. The problem, for which the solution is provided by the present invention, is to be able to define a set of nucleic acid probes that may be provided and the nucleotide composition of which makes it possible to obtain similar hybridization conditions for this set of probes, such that these probes are capable of hybridizing specifically to DNA-type and/or RNA-type target nucleic acids of set sequence, whatever their relative percentage of adenines and thymines, and also of guanines and cytosines.

In order to make the temperature for hybridization of all the probes, with target nucleic acids (DNAs or RNAs) of set sequence, the same while at the same time keeping an absolute hybridization specificity, whatever the relative percentage of adenines and thymines, and also of guanines and cytosines respectively paired, it is proposed here to use short probes which have deoxyinosines (dIs) instead of (dGs), not only to ensure specific pairing with dCs or Cs, but also to ensure this specific pairing with dCs or Cs by means of two hydrogen bonds, instead of the three hydrogen bonds formed between dG and dC or dG and C.

The number and the position of the dIs which replace the dGs in the sequences of the set probes are determined in such a way that the sequences of the set probes thus modified have a similar, preferably equal, content, with respect to one another, of guanines and cytosines, the hybridization of these modified probes thus resulting in the formation of DNA/DNA duplexes or of DNA/RNA heteroduplexes for which the Tm values are sufficiently similar to allow identical specific hybridization conditions for each of these probes.

The number and the position of the dIs which replace the dGs will in particular be determined by the number and the position, within the sequence of a given probe, of the pairings between dG and dC or dG and C, which replace pairings between dA and dT or dA and U of another given probe sequence.

Through the solution proposed here, the dI is not used as a nucleotide capable of pairing both with dC and with dA, dG and dT, or both with C and with A, G and U. In fact, although the dI is indeed capable of pairing with these deoxyribonucleosides and ribonucleosides, still by means of two hydrogen bonds, the pairing energy is very different according to the cases. By decreasing order of pairing energy, this will give dI:dC>dI:dA>dI:dG=dI:dT and dI:C>dI:A>dI:G=dI:U. In addition, according to the environment of dI, the pairing energy is not strictly identical, depending on whether this dI is positioned before or after dA, dG, dC, dT or another dI. However, in all cases, dI will always pair better with dC or C than with dT or U, the latter two hybridization possibilities always being the least favorable. With regard to the pairing properties of dI with the other deoxyribonucleotides, reference may be made, but without being limited thereto, to the articles by Case-Green et al. (Nucleic Acids Res., 1994, 22(2):131-136) and by Martin et al. (Nucleic Acids Res., 1995, 13(24):8927-8938) and to the documents which are referenced therein.

Thus, in a first aspect, a subject of the present invention is a method for analyzing a sample containing a target polynucleotide (within a DNA or RNA molecule) and/or one of its variants, said variant comprising one or more base substitutions with respect to said target polynucleotide, said method comprising the following steps:

a) providing the sample containing said target polynucleotide, or one of its variants, and at least two different oligodeoxyribonucleotides, hereinafter referred to by the general term "probes", the latter being arranged either in a distinct manner on a solid support, or contained in the same reactor, or alternatively distributed in a distinct manner on a device comprising a set of reactors, each of said probes having a sequence capable of forming a specific duplex with the target polynucleotide or one of its expected variants;

b) incubating said target polynucleotide, or one of its variants, with said probes under specific hybridization conditions for obtaining the formation of a duplex between said polynucleotide, or one of its expected variants, and one of said probes, even if said target polynucleotide and one of its expected variants differ from one another by only a single nucleotide; and c) detecting the duplexes formed on said solid support, or alternatively formed in solution in said same reactor or formed in solution in each of the reactors of said set of reactors, characterized in that at least one of the nucleotides dG in at least one of said probes has been substituted with a nucleotide dI, such that the specific hybridization conditions for obtaining the formation of a duplex between said target polynucleotide, or one of its expected variants, and one of said probes in step b) are identical for each said of probes.

Preferably, the invention relates to a method of analysis according to the present invention, characterized in that, in step a), said at least two different probes are arranged in a distinct manner on a solid support, or contained in solution in the same reactor, or alternatively distributed in solution in a distinct manner on a device comprising a set of same reactors, and in that, in step c), respectively, the duplexes formed are detected on the solid support, or the duplexes formed in solution are detected in said same reactor (or using an aliquot contained in this same reactor) or in each of the reactors of said set of same reactors.

The term "set of reactors" is intended to denote, in the present description, a set of reactors, preferably of same reactors, more preferably grouped together in one or, according to the number of reactors, in several same devices, and where the same hybridization conditions will be applied for each of the reactors of this set.

In a preferred embodiment, when the number of reactors is greater than one, the number of reactors is equal to the number of said different probes.

More preferably, this set of reactors may be provided, according to the size and/or the number of the reactors, in the form of one or more same plates or microplates on which will be arranged containers, cupules or wells in which the incubation of said target polynucleotide, or one of its variants, with said probes will be carried out in liquid medium.

In this first aspect, a particular subject of the present invention is a method for analyzing a sample containing a target polynucleotide and/or one of its variants, said variant comprising one or more base substitutions with respect to said target polynucleotide, said method comprising the following steps:

a) providing the sample containing said target polynucleotide, or one of its variants, and at least two different oligodeoxyribonucleotides, hereinafter referred to by the general term "probes", the latter being arranged in a distinct manner on a solid support, each of said probes having a sequence capable of forming a specific duplex with the target polynucleotide or one of its expected variants;

b) incubating said target polynucleotide, or one of its variants, with said probes under specific hybridization conditions for obtaining the formation of a duplex between said target polynucleotide, or one of its expected variants, and one of said probes, even if said target polynucleotide and one of its expected variants differ from one another by only a single nucleotide; and c) detecting the duplexes formed on the solid support, characterized in that at least one of the nucleotides dG in at least one of said probes has been substituted with a nucleotide dI, such that the specific hybridization conditions for obtaining the formation of a duplex between said target polynucleotide, or one of its expected variants, and one of said probes in step b) are identical for each of said probes.

The term "nucleic acid", "nucleic acid probe", "nucleic acid sequence", "polynucleotide", "oligonucleotide", "polynucleotide sequence" or "nucleotide sequence", and in the absence of any other specification, is here intended to denote a precise chain of modified or unmodified nucleotides making it possible to define a fragment or a region of a nucleic acid, which may or may not comprise nucleotides other than dA, dT, dG, dC or A, U, G and C, and which may correspond both to a double-stranded DNA or a single-stranded DNA and to products of transcription of said DNAs, such as RNAs.

The term "probe" will here be intended to denote an oligodeoxyribonucleotide used as a probe.

The term "small-size probes" will here be intended to denote probes whose size is sufficiently short to allow specific hybridization and discrimination between two different target polynucleotides, even if this difference relates to only one base. Preferably, these probes will be less than 40 nucleotides in length, and even more preferably less than 35, 30, 25, 24, 23, 22 or 21 nucleotides in length. More preferably, said probes will comprise at least 10 nucleotides, and even more preferably 11, 12, 13, 14, 15, 16, 17, 18, 19 or 20 nucleotides.

The term "target oligonucleotide" will here be intended to denote an oligonucleotide that it is intended to detect and/or identify and/or quantify in a sample, as opposed to the term "probe", a target oligonucleotide generally derived from an integral part of a DNA or of an RNA extracted from a biological sample, from tissue, from cells or from microorganisms such as bacteria, yeast, fungi, algae or else viruses or phages.

The expression "target oligonucleotide derived from a DNA or from an RNA" will here be intended to denote an oligonucleotide (single-stranded DNA or single-stranded RNA) for which the sequence is identical or complementary to 100% of the sequence of said DNA, or of said RNA, or of the sequence of one of their fragments.

The expression "variant or expected variant of a target oligonucleotide" will here be intended to denote an oligonucleotide for which the sequence comprises one or more base substitutions with respect to said target oligonucleotide, this being a variant for which it is sought to detect and/or identify and/or quantify the presence in a sample.

The term "duplex" is intended to denote, in the present description, a double-stranded nucleic acid resulting from the specific hybridization between two strictly or not strictly complementary DNA strands (DNA/DNA homoduplex) or between a DNA strand and an RNA strand which is strictly or not strictly complementary thereto (DNA/RNA heteroduplex). In the present description, only the nucleotides dC or C will be considered as being complementary to dI.

The term "RNA editing" or, more simply, the term "editing" is intended to denote, in the present invention, the deamination of adenosines (A) to inosines (I), within an RNA sequence, by adenosine deaminases whose activity depends on the double-stranded RNA; these adenosine deaminases are ADARs (RNA-dependent adenosine deaminases) according to whether the target RNA is an mRNA, or else ADATs (tRNA-dependent adenosine deaminases) according to whether the target RNAs are tRNAs (for review see Maas et al. BioEssays, 2000, 22(9), 790-802, and Reenan, TRENDS in Genetics, 2001, 17(2), 53-56, and Gerber et al. TRENDS in Biochemical Sciences, 2001, 26(6), 376-384, and Baas, Ann. Rev. Biochem. 2002, 71, 817-846, with the articles which are referenced therein).

The term "edited RNA" is intended to denote, in the present description, any RNA sequence in which at least one adenosine has been deaminated to inosine by an adenosine deaminase.

In a preferred embodiment, the number and the location of the substitutions of nucleotide dG with a nucleotide dI on said probes are determined such that the melting temperatures (Tm) of the duplexes which may be formed between one of said probes and said target polynucleotide, or one of its expected variants, are identical or sufficiently similar to allow said duplexes to be obtained by specific hybridization under the same hybridization conditions for each of said probes. Preferably, the maximum differences in the Tm values between said duplexes will be at most 10° C., and even more preferably 9, 8, 7, 6 or 5° C., or less.

The methods for measuring Tm values for double-stranded DNA are long-established and well known to those skilled in the art. They will not be developed here, but reference may be made, as a matter of interest, to Lehman et al. (J. Chem. Phys. 1968, 4(7):3170-3179), Crothers (Biopolymers, 1968, 6(10): 1391-1404) and, for a review, Lazurlin et al. (Biopolymers, 1970, 9(11): 1253-1306).

In an embodiment that is also preferred, the number and the location of the substitutions of nucleotide dG with a nucleotide dI on said probes are determined such that the number of remaining dGs capable of pairing with dC or with C in said duplexes is, preferably, identical or hardly different for each of said probes. More preferably, the difference between the number of remaining dGs capable of pairing with dC or with C in said duplexes is less than 10% of the total length of said duplex.

In an embodiment that is also preferred, said target polynucleotide or one of its expected variants is of the single-stranded DNA or single-stranded RNA type.

In an embodiment that is also preferred, said probes comprise a small number of bases, preferably 30 bases or fewer than 30 bases, preferably 25 bases or fewer than 25 bases, even more preferably 20 bases or fewer than 20 bases.

In an embodiment that is also preferred, said probes and said target polynucleotides, or one of their expected variants, use an identical number of bases or a number of bases that differs by one unit or, at most, by 10%.

In an embodiment that is also preferred, said target polynucleotide, or one of its expected variants, is prelabeled with a label capable of producing, directly or indirectly, a detectable signal, preferably a signal detectable by fluorescence or by measuring radioactivity when said probes are arranged on a solid support.

For example, said labels, when they are fluorescent, can be chosen from fluorochromes, in particular derived from cyanin, such as the fluorochromes Cy5 or Cy3.

In an embodiment that is also preferred, the specific pairing of the probe with said target polynucleotide is demonstrated by using a compound capable of being detected by molecular energy transfer, in particular by fluorescence energy transfer (called "FRET" for fluorescence resonance energy transfer).

By means of the "FRET" technique, the specific pairing of the probe with said target polynucleotide or one of its variants may, for example, be visualized by means of a pair of fluorophores, the first fluorophore being either a photon acceptor or photon donor and being located in the 5' position or in the 3' position of the probe, the second fluorophore then being, respectively, either a photon donor or a photon acceptor, and being positioned, respectively, in the 3' position or in the 5' position of the second probe; this second probe is defined such that it can hybridize, in a strictly identical manner, to a sequence identical and adjacent to said target polynucleotides, and such that the second fluorophore, which is a photon donor or photon acceptor, is positioned at a distance sufficiently close to the first fluorophore to ensure the transfer of energy from the donor fluorophore to the acceptor fluorophore. .

In the methods of analysis or processes of the invention, the labels and the techniques for detecting and/or quantifying the presence of duplexes formed on a solid support coated with probes, or formed in a homogeneous liquid phase, are well known to those skilled in the art and will not be developed here.

For the label systems allowing the detection of a hybridization between two polynucleotides in a homogeneous liquid phase by molecular energy transfer, in particular by "FRET", reference may, for example, be made, but without being limited thereto, to the article by Livak et al. (PCR Methods. Appl. 1995, 4:357-362) and to U.S. Pat. No. 6,117, 637 and to the documents which are referenced therein.

In an embodiment that is also preferred, said solid support is a solid support which can, where appropriate be activated or functionalized in order to ensure covalent attachment of said probes, in particular chosen from solid supports made of glass, plastic, Nylon®, silicone, silicon, or else polysaccharides or poly(heterosaccharides), such as cellulose, preferably made of glass, it being possible for the latter to be silanized.

In an embodiment that is also preferred, said probes may be functionalized by means of a function capable of reacting with said solid support so as to form a covalent bond with said support, it being possible for the latter to be activated, functionalized or else equipped with a spacer agent.

In an embodiment that is also preferred, said sample to be analyzed contains said target polynucleotide and at least one of its expected variants.

In an embodiment that is also preferred, the number of said different probes is at least equal to 3, 4, 5, 6, 7, 8, 9, 10, 15, 20 and 25, or alternatively at least equal to the number of expected variants of said target polynucleotide, at least one of which is liable to be present in said sample to be analyzed, said number of variants being at least equal to 2.

In an embodiment that is also preferred, the number of said probes in which at least one of the nucleotides dG has been substituted with a nucleotide dI is at least equal to 2, preferably to 3, 4, 5, 6, 7, 8, 9, 10 or 15, or alternatively to the number of expected variants of said target polynucleotide comprising a nucleotide dC or C instead of another nucleotide present in said target polynucleotide.

In another aspect, a subject of the present invention is an array of at least two different oligodeoxyribonucleotide probes, characterized in that at least one of the nucleotides dG on at least one of said probes has been substituted with a nucleotide dI, such that the hybridization conditions are identical for each of said probes, the latter containing a sequence capable of forming a specific duplex with a target polynucleotide, or one of its variants.

Preferably, the array of at least two probes according to the invention is characterized in that the number and the location of the substitutions of nucleotide dG with a nucleotide dI on said probes are determined such that the Tm values of the duplexes which may be formed with each of said probes are identical or sufficiently close to make it possible to obtain said duplexes by specific hybridization under the same hybridization conditions for each of said probes.

Also preferably, the array of at least two different probes according to the invention is characterized in that the number and the location of the substitutions of nucleotide dG with a nucleotide dI on said probes are determined such that the number of remaining dGs capable of pairing with dC or with C in said duplexes is identical or hardly different for each of said probes.

Also preferably, the array of at least two different probes according to the invention is characterized in that said probes are of the single-stranded DNA type.

Also preferably, the array of at least two different probes according to the invention is characterized in that said probes comprise a small number of bases, preferably 30 bases or fewer than 30 bases, preferably 25 bases or fewer than 25 bases, even more preferably 20 bases or fewer than 20 bases.

Also preferably, the array of at least two different probes according to the invention is characterized in that said probes use an identical number of bases or a number of bases that differs by one unit or, at most, by 10%.

In an embodiment that is also preferred, the number of said different probes is at least equal to 3, 5, 7, 10, 15, 20 and 25, or alternatively at least equal to the number of expected variants of said target polynucleotide, at least one of which is liable to be present in said sample to be analyzed, said number of variants being at least equal to 2.

Also preferably, the array of at least two different probes according to the invention is characterized in that the number of said probes in which at least one of the nucleotides dG has been substituted with a nucleotide dI is at least equal to 2, preferably to 3, 4, 5, 6, 7, 8, 9, 10 or 15, or alternatively to the number of expected variants of said target polynucleotide comprising a nucleotide dC or C instead of another nucleotide present in said target polynucleotide.

In a particularly preferred aspect, a subject of the present invention is an array of at least two different probes according to the invention, characterized in that said array consists of or comprises a set of probes for detecting and/or quantifying, in a sample, the presence of a target oligonucleotide, and a set of expected variants.

Preferably, said target oligonucleotide is derived from a gene fragment which may comprise—or the transcription product of which may comprise—at least one base substitution in the sequence from which said target oligonucleotide derives.

Also preferably, said target oligonucleotide is derived from an mRNA fragment which may comprise at least one editing site in the sequence of this fragment.

Even more preferably, said target oligonucleotide is derived from an mRNA fragment of a membrane receptor from a eukaryotic cell, in particular from a mammal, including the serotonin 5-HT$_{2C}$ receptor (5-HT$_{2C}$-R) or the glutamate receptor B subunit (GluR-B), 5-HT$_{2C}$-R being the most preferred.

In an embodiment that is also preferred, a subject of the invention is an array of at least two different probes according to the invention, characterized in that said array consists of or comprises a set of distinct probes for detecting and/or quantifying, in a sample, the potential presence of any target oligonucleotide derived from an mRNA fragment, which may or may not be edited.

In a particularly preferred embodiment, a subject of the present invention is an array of at least two different probes according to the invention, characterized in that said array consists of or comprises at least one set of distinct probes for detecting and/or quantifying, in a sample, the potential presence of the target polynucleotide derived from the unedited mRNA fragment and of any target polynucleotide derived from an mRNA fragment the editing of which may result in a modification of the amino acid sequence of the protein which is the product of translation of the unedited mRNA.

In an even more preferred embodiment, a subject of the present invention is an array of at least two different probes according to the invention, characterized in that said array consists of or comprises a set of thirty-two distinct probes for detecting and/or quantifying, in a sample, any target oligonucleotide derived from a fragment comprising the sequence SEQ ID No. 33 (5'-AUA CGU MU CCU A-3') of the edited or unedited mRNA of 5-HT$_{2C}$-R.

In this particular case, the expression "any target oligonucleotide derived from a 5-HT$_{2C}$-R mRNA fragment, said fragment comprising the sequence SEQ ID No. 33 (5'-AUA CGU MU CCU A-3') of the edited or unedited mRNA" is intended to denote:

any of the oligonucleotides of the set of oligonucleotides consisting of the thirty-two antisense RNAs, i.e. 100% complementary to the 5-HT$_{2C}$-R mRNA fragment, said fragment comprising the sequence SEQ ID No. 33, and in which SEQ ID No. 33, each nucleotide A corresponding to an editing site (nucleotides at position 1, 3, 7, 8 or 13 of SEQ ID No. 33) may or may not be edited; or any of the oligonucleotides of the set of oligonucleotides consisting of the thirty-two DNAs, i.e. 100% complementary to the 5-HT$_{2C}$-R mRNA fragment, said fragment comprising the sequence SEQ ID No. 33, and in which SEQ ID No. 33, each nucleotide A corresponding to an editing site (nucleotides at position 1, 3, 7, 8 or 13 of SEQ ID No. 33) may or may not be edited.

In an even more preferred embodiment, a subject of the present invention is an array of at least two different probes according to the invention, characterized in that said array consists of or comprises the following sets of probes:

the set of the thirty-two probes of sequence comprising the sequences of the fragments from nucleotide 3 to nucleotide 15 of SEQ ID Nos. 1 to 32, the parts of these probes located outside said fragment from nucleotide 3 to nucleotide 15 being identical to the corresponding parts (in DNA) of the 5-HT$_{2C}$-R mRNA; or the set of the thirty-two probes of sequence SEQ ID Nos. 1 to 32.

According to another aspect, a subject of the present invention is a biochip comprising an array of at least two different probes according to the present invention, placed on the same solid support, it being possible for said solid support to be, where appropriate, activated or functionalized so as to ensure covalent attachment of said probes, and in particular chosen from the solid supports as described above.

In another aspect, a subject of the present invention is a reactor comprising, in solution, an array of at least two different probes according to the present invention.

In another aspect a subject of the present invention is a device, in particular a plate or a microplate, consisting of at least two containers or cupules, said device comprising an array of at least two different probes according to the present invention, each of the containers or cupules containing one of said probes.

Preferably, the present invention relates to a biochip in which said probes are attached to said solid support, in particular by covalent bonding.

In another aspect, a subject of the present invention is a kit of reagents for detecting, or qualitatively or quantitatively analyzing target nucleic acids in a sample, characterized in that it comprises an array of at least two different probes according to the present invention and/or a biochip according to the invention.

According to yet another aspect, a subject of the present invention is a method for detecting and/or quantifying target oligonucleotides in a sample, characterized in that it comprises the following steps:

a) depositing the sample containing said target oligonucleotides, the detection of whose presence is sought, on a biochip according to the invention, or else in each of the containers or cupules of the device according to the invention, under the conditions for the specific hybridization of said target oligonucleotides with said probes;

b) where appropriate, rinsing the biochip obtained in step a) under the conditions for removing the nucleic acids of the sample that have not been captured by hybridization; and c) detecting and/or quantifying the target oligonucleotides captured by each of said probes by specific hybridization.

The present invention also comprises a method for detecting and/or quantifying target oligonucleotides in a sample, said target oligonucleotide being derived from an mRNA fragment which may comprise at least one editing site in the sequence of the fragment from which said target oligonucleotide is derived, characterized in that it comprises the following steps:

a) depositing the sample containing said target oligonucleotides, the detection of whose presence is sought, on a biochip covered with an array of probes according to the invention, or else in each of the containers or cupules of the device according to the invention, under the conditions for the specific hybridization of said target oligonucleotides with said probes;

b) where appropriate, rinsing the biochip obtained in step a) under the conditions for removing the nucleic acids of the sample that have not been captured by hybridization; and c) detecting and/or quantifying the target oligonucleotides captured by each of said probes by specific hybridization.

The present invention also comprises a method for detecting and/or quantifying any target oligonucleotide derived from an mRNA fragment which may comprise at least one editing site in the sequence of the fragment from which said target oligonucleotide is derived, characterized in that it comprises the following steps:

a) depositing the sample containing said target oligonucleotides, the detection of whose presence is sought,
either on a biochip covered with an array of probes according to the invention, or else
in each of the containers or cupules of the device according to the invention, in particular in each of the cupules of a microplate, consisting of at least two cupules, said microplate comprising an array of probes according to the present invention, each of the cupules containing just one of said probes, under the conditions for the specific hybridization of said target oligonucleotides with said probes, said array of probes consisting of or comprising a set of distinct probes capable of detecting and/or quantifying, in a sample, the potential presence of any target oligonucleotide derived from an mRNA fragment which may or may not be edited;

b) where appropriate, rinsing the biochip obtained in step a) under the conditions for removing the nucleic acids of the sample that have not been captured by hybridization; and c) detecting and/or quantifying the target oligonucleotides captured by each of said probes by specific hybridization.

The present invention also comprises a method for detecting and/or quantifying any target oligonucleotide present in a sample and derived from a fragment comprising the sequence SEQ ID No. 33 (5'-AUA CGU MU CCU A-3') of the edited or unedited mRNA of 5-HT$_{2C}$-R, characterized in that it comprises the following steps:

a) depositing the sample containing said target oligonucleotides, the detection of whose presence is sought,
either on a biochip covered with an array consisting of a or comprising the set of thirty-two distinct probes according to the invention, or else
in each of the containers or cupules of the device according to the invention, this device comprising an array consisting of a or comprising the set of thirty-two distinct probes according to the invention, in particular in each of the cupules of a microplate comprising 32 cupules, each of these cupules containing just one of said probes of the set of thirty-two probes, the set of thirty-two probes making it possible to detect and/or quantify, in a sample, any target oligonucleotide derived from a 5-HT$_{2C}$-R mRNA fragment, said fragment comprising the sequence SEQ ID No. 33 (5'-AUA CGU MU CCU A-3'), which may or may not be edited, under the conditions for the specific hybridization of said target oligonucleotides with said probes;

b) where appropriate, rinsing the biochip obtained in step a) under the conditions for removing the nucleic acids of the sample that have not been captured by hybridization; and c) detecting and/or quantifying the target oligonucleotides captured by each of said probes by specific hybridization.

In yet another aspect, the present invention also comprises a method for determining, in a sample, the percentage of each of the edited and unedited forms of the mRNA which may comprise at least one editing site, relative to the total amount of the edited or unedited mRNA forms present in said same sample (called "editing rate"), characterized in that it comprises a method according to the invention for detecting and/or quantifying any target oligonucleotide present in a sample and derived from an mRNA fragment which may or may not be edited, and in which method, at the end of step c), the ratio, expressed as a percentage, of the amount of oligonucleotides captured by a probe to the total amount of oligbnucleotides captured by the set of probes is determined for each of said probes.

In a particularly preferred embodiment of the above methods according to the invention, the target oligonucleotides are antisense mRNAs or complementary DNAs of the fragments of said edited or unedited mRNA, and said probes are DNAs corresponding to the sequences of the fragment of said edited or unedited mRNA.

In an equally preferred embodiment of the above methods according to the invention, said fragments from which the target oligonucleotides derive are fragments of nucleic acids extracted from a biological sample from a eukaryotic organism, in particular mammal, including human being.

In an embodiment that is also preferred, the target oligonucleotides used in the methods according to the invention are prelabeled with a label capable of producing, directly or indirectly, a detectable signal, preferably a fluorescent or radioactive signal.

In yet another aspect, the present invention also comprises the use of a biochip or of a device according to the invention as an affinity matrix, for purifying nucleic acids or for sequencing nucleic acids.

The present invention also comprises the use of a biochip or a device according to the invention, for detecting and/or studying genetic polymorphisms, in particular SNP (single nucleotide polymorphism) or for qualitatively or quantitatively analyzing gene expression.

For example, but without being limited thereto, it is possible to deposit on the biochips or in the containers, in particular cupules of the devices according to the invention, DNA probes corresponding to a known gene of interest. Each deposit may contain a probe corresponding to a gene and, from one deposit to another, the probes will correspond to said gene exhibiting a polymorphism.

The genomic DNA or RNA or the mRNA, or their fragments, of the tissue, of the cell or of the microorganisms that it is desired to study may be extracted and then labeled, for example with fluorochromes or with radioactive compounds (the DNAs may be amplified by PCR and the RNAs or mRNAs may in particular be converted to complementary DNAs (cDNA) by reverse transcription and, where appropriate, amplified by RT-PCR techniques, or else converted to antisense RNA).

These antisense RNAs or cDNAs will then be deposited on the biochip covered with the probes according to the invention and, where appropriate, may bind, by specific hybridization, with these probes, deposited beforehand, which correspond to them. The amount of signal, in particular of fluorescence or of radioactivity, thus corresponding to the amount of target nucleic acids hybridized, which will in particular be proportional to the initial amount of extracted mRNAs, if the target DNAs deposited are complementary cDNAs from reverse-transcribed mRNAs, will then be detected on each deposit or in each container. It will thus be possible to measure the transcription activity of the cell for certain genes.

There are, consequently, many applications for these DNA biochips or devices according to the invention, such as transcription studies, diagnosis (search for mutation), the search for therapeutic targets, or genotyping.

The present invention also comprises the use of a biochip or of a device according to the invention, for determining an mRNA editing rate.

The methods of analysis by means of processes using biochips or devices according to the invention in reagent kits according to the invention make it possible to demonstrate one or more base substitutions in a short DNA sequence. They also make it possible to reveal single nucleotide polymorphisms (SNPs). They also make it possible to measure the degree of mRNA editing, whether this editing is restricted to a single site or whether it affects several sites in the same mRNA molecule. In other words, they make it possible to reveal any mismatching, of one or more nucleotides, in a given short sequence whatever its base composition. By virtue of this characteristic, they therefore make it possible to put forward the diagnosis of a point mutation, just as they make it possible to detect the presence of pathogenic agents—which they make it possible to genotype—which may be viruses, prokaryotes or eukaryotes which infect humans, animals and plants. They also make it possible to analyze the transcnptome with short probes, according to a strategy that is different from those used up until now, since they do not make it necessary to have, between the various sequences, a constant percentage of paired guanines and cytosines. Finally, they make it possible to genotype individuals belonging either to the same species or to different species, in the context of comparative genomics.

In another aspect, a subject of the invention is an SSCP method for obtaining, under given analytical conditions, the editing profile of an mRNA which may be edited, using a specific tissue sample or using a sample of a population of eukaryotic cells, characterized in that it comprises the following steps:

a) extraction of the total RNAs of said sample, followed, where appropriate, by purification of the mRNAs;

b) reverse transcription of the RNAs extracted in step a) and synthesisrof the double-stranded DNA;

c) PCR amplification of the DNAs obtained in step b) using a pair of primers specific for said mRNA which may be edited, this pair of primers being chosen so as to be able to amplify all the editing forms potentially present in the RNA extract, these primers being labeled with fluorophores;

d) where appropriate, purification of the PCR products obtained in step c);

e) where appropriate, quantification of the PCR products obtained in step d);

f) dissociation of the double-stranded DNAs to single-stranded DNAs, in particular by heating followed by abrupt cooling;

g) separation of the single-stranded DNAs by capillary electrophoresis; and h) obtaining of the electrophoretic migration profile of the various single-stranded DNAs, referred to here as "editing profile", by reading of the fluorescence and, where appropriate, acquisition of the profile data by means of the exploitation system associated with the fluorescence reader.

The term "SSCP method" will be intended to denote, in the present description, a method based on the demonstration of single strand DNA conformation polymorphism (SSCP).

Preferably, in the SSCP method according to the invention, the pair of primers used in step c) is chosen such that the PCR products obtained are at least 100 bases in length, more preferably at least 125, 150, 175, 200, 225 or 250 bases in length, in order to allow folding characteristic of the editing form of each or of the two strands separated after step g).

Preferably, in the SSCP method according to the invention, said mRNA which may be edited is that of a membrane receptor, in particular the serotonin $5\text{-HT}_{2C}$-receptor ($5\text{-HT}_{2C}$-R) or that of the glutamate receptor B subunit (GluR-B), $5\text{-HT}_{2C}$-R being the most preferred.

Preferably, in the SSCP method according to the invention, said mRNA which may be edited is that of the membrane receptor $5\text{-HT}_{2C}$-R and the pair of primers is the following pair, preferably labeled with fluorophores:

PCR9    TGTCCCTAGCCATTGCTGATATGCT;    (SEQ ID No. 36)
and

PCR10  GCAATCTTCATGATGGCCTTAGTCCG.  (SEQ ID No. 37)

In another aspect, a subject of the invention is an SSCP method for obtaining, under given analytical conditions, the editing profile and the editing rate of an mRNA which may be edited, using a specific tissue sample or using a sample of a population of eukaryotic cells, characterized in that it comprises the following steps:

a) obtaining the editing profile by means of the SSCP method according to the invention above;

b) comparing the profile obtained in step a) with standard profiles corresponding to:

characteristic profiles obtained, under these given conditions, for each of the edited (or unedited) separate forms of said mRNA; and/or characteristic profiles of known qualitative and/or quantitative mixtures of each of these edited or unedited forms, obtained under these given conditions; and/or known editing profiles, under these same given conditions, of this same mRNA for normal patients or patients presenting confirmed pathologies, for mRNA extracts of said specific tissues, or else for said population of eukaryotic cells, the latter preferably having been cultured under conditions which make it possible to control the variations in editing rate of said mRNA;

c) selecting the known editing profile corresponding to the editing profile obtained in step a); and d) associating the editing rate of the profile selected in step c) with the editing profile obtained in step a).

In said SSCP method according to the invention above for obtaining both the editing profile and the editing rate of an mRNA, this method including step a) for obtaining the editing profile by means of the SSCP method according to the invention, the preferences indicated for the SSCP method (length of the PCR products, mRNA of a membrane receptor, in particular of $5\text{-HT}_{2C}\text{-R}$ or of the glutamate receptor B subunit (GluR-B), pair of primers SEQ ID No. 36 and SEQ ID No. 37 for the $5\text{-HT}_{2C}\text{-R}$ mRNA, labeling thereof) are also claimed here.

In yet another aspect, the present invention also comprises a method for selecting a compound capable of modulating the editing of an editing site located on a fragment of an mRNA present in a eukaryotic cell, in particular a mammalian cell, said edited mRNA sequence having the sequence given the notation "E" and said unedited mRNA fragment having the sequence given the notation "UE", characterized in that it comprises the following steps:

A) bringing said compound to be evaluated into contact with a population of eukaryotic cells expressing the gene of said mRNA capable of being edited;

B) demonstrating the modulation or non-modulation of the editing of the editing site of said mRNA in said cell using a sample of target oligonucleotides derived from said mRNA fragment and obtained from a nucleic acid extract derived from said cells obtained in step A), by means of a method according to the invention for detecting and/or quantifying target oligonucleotides in a sample, said target oligonucleotide being derived from an mRNA fragment which may comprise at least one editing site on the sequence of the fragment from which said target oligonucleotide is derived, and in which method at least two of said probes are two DNAs, one corresponding to the DNA sequence of said fragment "E" and the other corresponding to the DNA sequence of said fragment "UE";

C) where appropriate, in that, in step c) of the method mentioned above in step B), the detection and/or the quantification of the target oligonucleotides captured at each of said probes are compared with those obtained using a population of control cells; and D) selecting this compound if it modulates the editing of said editing site.

In this other aspect, the present invention also comprises a method for selecting compounds capable of modulating the editing rate of an mRNA fragment present in the eukaryotic cell, in particular a mammalian cell, characterized in that it comprises the following steps:

A) bringing said compound to be evaluated into contact with a population of eukaryotic cells expressing said mRNA capable of being edited;

B) demonstrating the modulation or non-modulation of the editing rate of said mRNA fragment in said cell using a sample of target oligonucleotides derived from said mRNA fragment and obtained from a nucleic acid extract derived from said cells obtained in step A), by means of a method according to the invention for detecting and/or quantifying any target oligonucleotide derived from an mRNA fragment which may comprise at least one editing site on the sequence of the fragment from which said target oligonucleotide is derived;

C) determining, at the end of step c) of the method mentioned above in step B) and for each of said probes, the editing rate corresponding to the ratio, expressed as a percentage, of the amount of oligonucleotides captured by a probe to the total amount of oligonucleotides captured by the set of probes;

D) where appropriate, in that the editing rate obtained is compared with that obtained for a population of control cells; and E) selecting this compound if it modulates the editing rate of said mRNA fragment.

Mood is that basic affective disposition which causes human beings to swing from the most extreme joy to the deepest pain, according to the events and emotions which control their responses, allowing them to adapt as well as possible to their social, affective, family and professional environment. The regulation of mood is a complex process which involves neuromediators belonging to the three monoaminergic systems, i.e. noradrenergic, serotoninergic and dopaminergic. These neuromediators act via receptors located in the plasma membrane. When these receptors are channel receptors, binding of the ligand modulates the activity thereof, whereas, when they are coupled to intracellular effectors, binding of the same ligands will result in a signal transduction through the plasma membrane. This signal transduction is the result of a conformational change in the receptor subsequent to the binding of the ligand to the extracellular portion of the receptor. The specificity of the cell's response to these neuromediators depends, firstly, on the nature of the receptor and therefore on the type of interaction that it will bring about inside the cell, subsequent to its conformational change and, secondly, on the nature of the biochemical reaction cascades thus induced, which will be specific to the type of cell concerned.

There is no receptor that is responsible, on its own, for regulating mood in response to a single neuromediator, all the more so since the expression of the genes of these receptors is interconnected. However, among the new antidepressants, referred to as "second generation"—they belong neither to the tricyclic antidepressant family nor to that of the monoamine oxidase inhibitors (MAOs)—some of them, such as fluvoxamine (Floxyfral™), fluoxetine (Prozac™) and paroxetine (Deroxat™), are considered to be powerful, and especially specific, inhibitors of serotonin recapture in the synaptic cleft (in this respect, see Goodnick et al. J. Psychopharmacol. 1998, 12(3) (Suppl B) S5-20). In other words, the antidepressants of this family act by causing an increase in the serotonin concentration in the synaptic cleft, thus forcing a signal transduction which will be too weak, either due to insufficiency of serotonin or due to insufficiency of serotonin receptors, in terms of number or of efficiency in transducing the signal.

Serotonin, or 5-hydroxytryptamine (5-HT), is a neuromediator which causes extremely varied physiological effects by binding to receptors of different subtypes. The $5\text{-HT}_2$ family of serotonin receptors belongs to the large group of trimeric G-protein-coupled receptors with seven transmembrane domains. This family comprises three receptor subtypes (5-HT$_{2A}$, 5-HT$_{2B}$ and 5-HT$_{2C}$) which, by means of Gq proteins, activate a phospholipase Cβ. The latter, once activated, hydrolyzes membrane phospholipids with, as a result, an increase in the intracellular concentrations of inositol phosphates (InsP) and the appearance of diacylglycerol (DAG), which remains associated with the plasma membrane. The 5-HT$_{2C}$ subtype receptors (5-HT$_{2C}$-R) are present in the central nervous system, including the cortex, the striatum, the hypothalamus, the olfactory bulb and the choroid plexus. 5-HT$_{2C}$-R is most certainly the or one of the serotonin receptors involved in regulating mood. It also appears to be involved in the perception of sexual desire (in this respect, see J. Lane, Psychopharmacol., 1997, 11(1):72-82), and in the feeling of hunger (in this respect, see Bickerdike et al., Diabetes, Obesity and Metabolism, 1999, 1:207-214). With regard to the classification of the receptors for serotonin of the 5-HT$_2$ family and their signal transduction mode, reference will be made to Baxter et al. (Trends Pharmacol. Sci., 1995, 16(3):105-110), and also to Roth et al. (Pharmacol. Ther., 1998, 79(3):231-257) and to the articles which are referenced therein. Similarly, for the pharmacological characterization of 5-HT$_2$ receptors, reference will be made to Jerman et al. (Eur. J. Pharm., 2001, 414:23-30) and to the articles which are referenced therein. Finally, the complete cDNA sequence for 5-HT$_{2C}$-R, the structure of its gene and the description of the alternative splicing of the primary transcript of the latter will be found in Xie et al. (Genomics, 1996, 35:551-561), and the corresponding sequences will be found in the GenBank/EMBL data banks under the No. U49516 for the cDNA and the No. U49648 for the sequences located in the 5' position of the gene.

In accordance with the functioning mode of trimeric Gq-protein coupled receptors with seven transmembrane domains, the aq subunit which activates a phospholipase Cβ, stimulation of 5-HT$_{2C}$-R by serotonin results in hydrolysis of phosphatidylinositol 4,5-bisphosphate (PIP2) to inositol-1,4,5-triphosphate (IP3) and DAG. The DAG thus produced in turn activates a protein kinase C which will result in a modification of gene expression by means of a cascade of biochemical reactions. The specificity of this modification of gene expression depends on the type of cell concerned. The IP3 produced by the hydrolysis of the PIP2 is a small water-soluble molecule which diffuses rapidly in the cytosol where it brings about a release of calcium from the endoplasmic reticulum through interaction with receptor channels. This sudden increase in intracytosolic calcium concentration results in an immediate cell response by modification of the activity of proteins whose presence produces the specificity of response of the cell type concerned. Two mechanisms control the arrest of the cell response by decreasing the intracytosolic calcium concentration. The first is the result of calcium being pumped out of the cytosol, mainly out of the cell, the second is the result of the rapid inactivation of IP3, mainly through it being dephosphorylated by specific phosphatases.

The IP3 dephosphorylation step is the target of this other pharmacological agent represented by the lithium salts, lithium carbonate (Teralithe®) and lithium gluconate (Neurolithium®). Lithium salts were used in the 1850s in the treatment of gout, and then at the end of the XIXth century in the treatment of mania, were forgotten up until the middle of the XXth century and have again been used, with remarkable success, since the beginning of the 1970s in the treatment of manic phases, in particular in manic depressive psychoses, where they also prove to be an effective prophylaxis for relapses of bipolar mood disorders. Lithium salts inhibit the activity of the inositol-1-phosphatase responsible for the entire dephosphorylation of IP3, which results in the formation and in the recycling of inositol, which is essential for PIP2 synthesis. Under these conditions, the decrease in PIP2 concentration at the intracellular face of the plasma membrane is nothing more than a decrease in the substrate for the activated phospholipase C-β, the result of which is an impairment of the effects of the activation of the trimeric Gq-protein-coupled receptors. In other words, the lithium salts would act, inter alia, by causing a decrease in available PIP2, thus impairing a signal transduction that was too great, either due to excess serotonin, or due to an excess of serotonin receptors, in terms of number and of efficiency in transducing the signal (as regards the current understanding of the mode of action of lithium salts, see Coyle et al., 2002, Nature Medicine, 8(6):557-558, with the articles referenced therein).

5-HT$_{2C}$-R therefore appears to be one of the key molecules of the serotonin response in the regulation of mood since it enables a response from the cell, the size of which depends on its efficiency in transducing the signal. There is only one 5-HT$_{2C}$-R gene, carried by the X chromosome, and therefore one allele of this gene in men and two in women, one of which is potentially inactive through inactivation of one of two X chromosomes. Consequently, it should be expected that only the extracellular serotonin concentration and the number of receptors present at the membrane at a given time contribute to the efficiency of signal transduction in response to serotonin. In fact, while the existence of differential splicing of the pre-mRNA of 5-HT$_{2C}$-R has been demonstrated, it appears that only one form of 5-HT$_{2C}$-R may have seven transmembrane domains and be active. However, there are at least twenty-four types of different receptors, products of expression of the same gene since they are the result of a mechanism of post-transcriptional regulation of gene expression, called editing.

Editing is the mechanism by which information contained in the gene is modified after transcription. The general term "mRNA editing" includes the modification of the sequence of these mRNAs which results in a change, in terms of nature or number, in the amino acids incorporated into the protein during translation, it no longer being possible for the sequence of the protein to be deduced from that of the gene which directs its synthesis. The premessenger RNA of 5-HT$_{2C}$-R can undergo a specific enzymatic modification of certain adenosines (A), in the portion of what will become the definitive mRNA which directs the incorporation of the amino acids located in the second intracellular loop of 5-HT$_{2C}$-R. In fact, the distal part of the fifth exon and the proximal part of the fifth intron of the primary transcript are capable of forming a stem-loop structure potentially recognized by two enzymes, ADAR1 and ADAR2 (double-stranded RNA-dependent adenosine deaminase), which make it possible to edit the premessenger RNA before it is spliced. This editing is produced by deamination of As, which are then converted to inosine (I). Once the splicing has been completed, the part of the mRNA which contained the As which underwent the editing now contains Is. When the 5-HT$_{2C}$-R mRNA is translated, it is thought that the Is are read as Gs. In fact, during in vitro synthesis of the cDNA from the 5-HT$_{2C}$-R mRNA that underwent the deamination of As to Is, the reverse transcriptase incorporates dCs opposite the Is, instead of dTs which should normally have been incorporated opposite the As. Consequently, during the synthesis of the second strand which results in the formation of the double-stranded cDNA, a dG is introduced opposite each dC incorporated into the first strand. Sequencing of the double-stranded cDNA thus obtained makes it possible to observe the replacement of the dAs with dGs, due to the initial deamination of the As to Is in the mRNA which underwent the editing. Consequently, the editing of the mRNA results in a modification of the meaning of the codons in which the As are replaced with Is, which are therefore thought to be read as Gs (more specifically, with regard to the editing of human 5-HT$_{2C}$-R, see Fitzgerald et al., Neuropsychopharmacology, 1999, 21(2S), 82S-90S).

Given that which has been described above concerning, firstly, the mode of action of second-generation antidepressants which act by increasing serotonin concentration by inhibiting its recapture and, secondly, the mode of action of lithium salts which act on mania by limiting the availability of PIP2, the degree (or rate) of editing of 5-HT$_{2C}$-R very certainly plays a role in the regulation of mood. In this respect, the study by Niswander et al. (Neuropsychopharmacol., 2001, 24:478-491), carried out post-mortem, demonstrated that 5-HT$_{2C}$-R mRNA editing, in particular at the A site, was statistically higher in the prefrontal cortex of the brain of patients who died through suicide than in the same area of the brain of patients who died for other reasons.

Mention may also be made of another study, carried out by Gurevich et al. (Neuron, 2002, 34(3):349-356), which demonstrated that the 5-HT$_{2C}$-R mRNA editing rate was increased on the E site (called "C" in the article) and decreased on the D site in the frontal cortex of the brain of patients who died through suicide, although they were suffering from major depression.

Conversely, Sodhi et al. (Mol. Psychiatry, 2001, 6(4):373-379) have shown that the 5-HT$_{2C}$-R mRNA editing rate is decreased in the frontal cortex of the brain of patients classified as schizophrenic.

Thus, an unedited receptor would result in a manic state, whereas a receptor that was too highly edited would result in a depressive state. In the light of this summary and of the interpretation thereof made by the inventor, it was concluded that a modulation of 5-HT$_{2C}$-R mRNA editing rate results in a modulation of mood, through a modification of the response of 5-HT$_{2C}$-R to stimulation by serotonin. Thus, an inhibition of 5-HT$_{2C}$-R editing rate would result in an increase in the response to stimulation by serotonin, whereas a stimulation of or an increase in 5-HT$_{2C}$-R mRNA editing rate would result in a decrease of this same response to stimulation by serotonin. This would, in general, result in an antidepressant effect for the compounds capable of inhibiting 5-HT$_{2C}$-R mRNA editing rate and in an inhibitory effect on mania for the compounds capable of stimulating or increasing 5-HT$_{2C}$-R mRNA editing rate.

Thus, in a particularly preferred embodiment, the present invention comprises a method for selecting a compound capable of modulating the editing rate of the RNA fragment comprising the sequence SEQ ID No. 33 (5'-AUA CGU MU CCU A-3') of the 5-HT$_{2C}$-R mRNA in a eukaryotic cell, in particular a mammalian cell, characterized in that it comprises the following steps:

A) bringing said compound to be evaluated into contact with a population of eukaryotic cells expressing the gene of said mRNA;

B) demonstrating the modulation or non-modulation of the editing rate of said mRNA fragment in said cell using a sample of target oligonucleotides derived from said mRNA fragment and obtained from a nucleic acid extract derived from said cells obtained in step A), by means of a method according to the invention for detecting and/or quantifying any target oligonucleotide present in a sample and derived from a fragment of the 5-HT$_{2C}$-R mRNA, said fragment comprising the sequence SEQ ID No. 33 (5'-AUA CGU MU CCU A-3') which may or may not be edited;

C) determining, at the end of step c) of the method mentioned above in step B) and for each of said probes, the editing rate corresponding to the ratio, expressed as a percentage, of the amount of oligonucleotides captured by a probe to the total amount of oligonucleotides captured by the set of probes;

D) where appropriate, in that the editing rate obtained is compared with that obtained for a population of control cells; and E) selecting this compound if it modulates the editing rate of said mRNA fragment.

In another aspect, a subject of the present invention is a method for selecting a compound capable of modulating the editing rate and/or editing profile of an mRNA capable of being edited in a specific tissue or a population of eukaryotic cells expressing the gene of said mRNA, in particular from a mammal, such as human or mouse, characterized in that it comprises the following steps:

a) bringing said compound to be evaluated into contact, in vivo or in cellulo, with said specific tissue or said population of eukaryotic cells;

b) obtaining the editing profile by means of the SSCP method according to the invention, under given analytical conditions;

c) comparing the profile obtained in step b) with:
 either standard profiles corresponding to known editing profiles of this same mRNA, for the same specific tissue or the same population of eukaryotic cells, under the same given analytical conditions,
 or an editing profile determined in parallel and obtained for the same specific control tissue or the same population of control eukaryotic cells that have not been brought into contact with the compound to be evaluated; and d) selecting said compound to be evaluated if the editing profiles compared in step c) are significantly different from one another.

In said above method for selecting a compound capable of modulating the editing rate and/or editing profile of an mRNA according to the invention and including, in step b), the obtaining of the editing profile by means of the SSCP method according to the invention, the preferences indicated for the SSCP method (length of the PCR products, mRNA of a membrane receptor, in particular of 5-HT$_{2C}$-R or of the glutamate receptor B subunit (GluR-B), pair of primers SEQ ID No. 36 and SEQ ID No. 37 for the 5-HT$_{2C}$-R mRNA, labeling thereof) are also claimed here.

In another aspect, a subject of the present invention is also a method for selecting a compound capable of preventing and/or treating, in a patient, a pathology associated, at least in part, with the editing of an mRNA capable of being edited, characterized in that it comprises the following steps:

a) bringing said compound to be evaluated into contact, in vivo or in cellulo, with a specific tissue or a population of eukaryotic cells expressing the gene of said mRNA capable of being edited, said specific tissue or said population of eukaryotic cells exhibiting, before being brought into contact with the compound to be tested, an editing profile of said mRNA characteristic of the associated pathology, under given analytical conditions;

b) obtaining the editing profile by means of the SSCP method according to the invention, under these given analytical conditions;

c) comparing the profile obtained in step b) with:
 α) a standard profile corresponding to a known editing profile of this same mRNA, for the same specific tissue or for the same population of cells, under the same given analytical conditions, this editing profile being representative of a normal patient or a patient not presenting said associated pathology; and, where appropriate, with:

β) an editing profile obtained for the same control specific tissue or for the same population of control cells that have not been brought into contact with the compound to be evaluated, under the same given analytical conditions; and d) selecting said compound to be evaluated if the editing profiles compared in step c) show that the one obtained in step b) is significantly identical to the one in step c)α), and, where appropriate, confirming this selection if the profile obtained in step b) is significantly different from the one in step c)β).

In said above method for selecting a compound capable of preventing and/or treating, in a patient, a pathology associated with the editing of an mRNA according to the invention and including, in step b) the obtaining of the editing profile by means of the SSCP method according to the invention, the preferences indicated for the SSCP method (length of the PCR products, mRNA of a membrane receptor, in particular of 5-$HT_{2C}$-R or of the glutamate receptor B subunit (GluR-B), pair of primers SEQ ID No. 36 and SEQ ID No. 37 for the 5-$HT_{2C}$-R mRNA, labeling thereof) are also claimed here.

In a particular aspect, a subject of the present invention is a method for selecting a compound capable of preventing and/or treating, in a patient, a pathology associated, at least in part, with the editing or nonediting of an mRNA capable of being edited, with the same therapeutic mechanism or effectiveness as a compound known to modulate the editing profile of said RNA and known to prevent and/or treat, in a patient, the same associated pathology, characterized in that it comprises the following steps:

a) bringing said compound to be evaluated into contact, in vivo or in cellulo, with a specific tissue or a population of eukaryotic cells expressing the gene of said mRNA capable of being edited, said specific tissue or said population of eukaryotic cells exhibiting, before being brought into contact with the compound to be tested, an editing profile of said mRNA characteristic of the associated pathology, under given analytical conditions;

b) obtaining the editing profile by means of the SSCP method according to the invention, under these given analytical conditions;

c) comparing the profile obtained in step b) with:

α) a standard profile corresponding to a known editing profile of this same mRNA, for the same specific tissue or for the same population of cells having been brought into contact, in vivo or in cellulo, with said compound known to modulate the editing profile of said RNA, under the same given analytical conditions, and known to prevent and/or treat, in a patient, the same associated pathology; and, where appropriate, with:

β) an editing profile obtained for the same control specific tissue or for the same population of control cells that have not been brought into contact with the compound to be evaluated, under the same given analytical conditions; and d) selecting said compound to be evaluated if the editing profiles compared in step c) show that the one obtained in step b) is significantly identical to the one in step c)α), and, where appropriate, confirming this selection if the profile obtained in step b) is significantly different from the one in step c)β).

In said above method for selecting a compound capable of preventing and/or treating, in a patient, a pathology associated, at least in part, with the editing or nonediting of an mRNA capable of being edited, with the same therapeutic mechanism or effectiveness as a known compound according to the invention and including, in step b), the obtaining of the editing profile by means of the SSCP method according to the invention, the preferences indicated for the SSCP method (length of the PCR products, mRNA of a membrane receptor, in particular of 5-$HT_{2C}$-R or of the glutamate receptor B subunit (GluR-B), pair of primers SEQ ID No. 36 and SEQ ID No. 37 for the 5-$HT_{2C}$-R mRNA, labeling thereof) are also claimed here.

In yet another aspect, a subject of the present invention is a method for diagnosing, where appropriate for predicting, a disease associated, at least in part, with an mRNA capable of being edited, using a tissue or cell sample taken from a patient to be tested, characterized in that it comprises the following steps:

a) obtaining the editing profile of said mRNA by means of the SSCP method according to the invention, under given analytical conditions;

b) comparing the profile obtained in step a) with standard profiles corresponding to known editing profiles of this same mRNA for normal patients or patients presenting confirmed pathologies, for mRNA extracts of the same tissue or of the same cell, under these same given conditions, or else for cells derived from cell lines; and c) selecting the known editing profile corresponding to the editing profile obtained in step a); and d) associating the diagnosis related to the profile selected in step c), with the patient tested.

In said above method for diagnosing a disease associated, at least in part, with an mRNA according to the invention and including, in step a), the obtaining of the editing profile by means of the SSCP method according to the invention, the preference is indicated for the SSCP method (length of the PCR products, mRNA of a membrane receptor, in particular of 5-$HT_{2C}$-R or of the glutamate receptor B subunit (GluR-B), pair of primers SEQ ID No. 36 and SEQ ID No. 37 for the 5-$HT_{2C}$-R mRNA, labeling thereof) are also claimed here.

According to another particular aspect, the present invention comprises a first method for selecting a compound capable of modulating the editing rate of the RNA fragment comprising the sequence SEQ ID No. 33 (5'-AUA CGU MU CCU A-3') of the 5-$HT_{2C}$-R mRNA according to the invention, or a second method for selecting a compound capable of modulating the editing rate and/or the editing profile of the 5-$HT_{2C}$-R mRNA according to the invention including, in step b), said SSCP method for obtaining the editing profile, characterized in that, in step E) of the first method mentioned according to the invention, or in step d) of the second method mentioned according to the invention, the compound is selected if it does not also modulate the editing rate or the editing profile of the glutamate receptor B subunit (GluR-B) mRNA.

According to another particular aspect, the present invention comprises a first method for selecting a compound capable of modulating the editing rate of the RNA fragment comprising the sequence SEQ ID No. 33 (5'-AUA CGU MU CCU A-3') of the 5-$HT_{2C}$-R mRNA according to the invention, or a second method for selecting a compound capable of modulating the editing rate and/or the editing profile of the 5-$HT_{2C}$-R mRNA according to the invention including, in step b), said SSCP method for obtaining the editing profile, characterized in that, in step E) of the first method mentioned according to the invention, or in step d) of the second method mentioned according to the invention, the compound is selected if it decreases the editing rate of at least one editing site of said RNA fragment, which editing site, when it is edited, modifies the sequence of the amino acids of the second intracellular loop of 5-$HT_{2C}$-R, in particular if this decrease in editing rate increases the ability of the cells expressing the 5-$HT_{2C}$-R gene to respond to a stimulation by serotonin.

In another particular aspect, the present invention comprises a first method for selecting a compound capable of modulating the editing rate of the RNA fragment comprising the sequence SEQ ID No. 33 (5'-AUA CGU MU CCU A-3') of the 5-HT$_{2C}$-R mRNA according to the invention, or a second method for selecting a compound capable of modulating the editing rate and/or the editing profile of the 5-HT$_{2C}$-R mRNA according to the invention including, in step b) said SSCP method for obtaining the editing profile, characterized in that in step E) of the first method mentioned according to the invention, or in step d) of the second method mentioned according to the invention, the compound is selected if it increases the editing rate of at least one editing site of said RNA fragment, which editing site, when it is edited, modifies the sequence of the amino acids of the second intracellular loop of 5-HT$_{2C}$-R, in particular if this increase in editing rate decreases the ability of the cells expressing the 5-HT$_{2C}$-R gene to respond to a stimulation by serotonin.

In yet another aspect, the present invention comprises the use of a compound capable of modulating the editing rate of the 5-HT$_{2C}$-R mRNA, said compound having been selected or being capable of being selected by means of a method for selecting a compound capable of modulating the editing rate of the 5-HT$_{2C}$-R mRNA in a eukaryotic cell, in particular a mammalian cell, according to the invention, for preparing a pharmaceutical composition intended to modulate mood in a patient requiring such a treatment, in particular for preparing a pharmaceutical composition intended either for the treatment of depression if this selected compound decreases the editing rate of said editing site, or for the treatment of mania or of certain forms of schizophrenia if this selected compound increases the editing rate of said editing site.

According to yet another aspect, a subject of the present invention is a compound having activity that modulates the editing rate of the RNA fragment comprising the sequence SEQ ID No. 33 (5'-AUA CGU MU CCU A-3') of the 5-HT$_{2C}$-R mRNA, for the treatment of mood.

For mood disorders which can be improved with medicinal products that modulate 5-HT$_{2C}$-R editing, reference may be made to the manual "Diagnostic and Statistical Manual of Mental Disorders, fourth edition, text revision, published by the American Psychiatric Association, Washington D.C., 2000, DSM-1V™".

For depressions, mention may particularly be made of:
  major depression characterized by one or more depressive episodes (i.e. at least 2 weeks of depressive mood with a loss of interest accompanied by at least 4 additional symptoms of depression) (see DSM-IV p 349-369);
  bipolar depression:
    bipolar I: characterized by one or more manic or mixed episodes, generally accompanied by major episodes of depression (see DSM-IV p 382),
    bipolar II: characterized by one or more episodes of major depression accompanied by at least one hypomanic episode (see DSM-IV p 392), and
  cyclothymic disorders: characterized by at least two weeks of numerous periods of hypomanic symptoms and of depressive symptoms (see DSM-IV p 398);
  melancholy: melancholic states are encountered in individuals suffering from major depression and in individuals suffering from bipolar depression. This state is characterized by a loss of interest and/or of pleasure in all activities, and also by a decrease in reactivity to stimuli that usually trigger pleasure (see DSM-IV p 419); and
  schizophrenia: characterized by disorders lasting at least six months and including at least one month of positive symptoms (delusions, hallucination, language disorganization) and negative symptoms (of depressive type) (see DSM-IV p 298).

In this other aspect, a particular subject of the present invention is a compound capable of decreasing the editing rate of at least one editing site of the RNA fragment comprising the sequence SEQ ID No. 33 (5'-AUA CGU AAU CCU A-3') of the 5-HT$_{2C}$-R mRNA, which editing site, when it is edited, modifies the sequence of the amino acids of the second intracellular loop of 5-HT$_{2C}$-R, for the treatment of depression, in particular if this decrease in editing rate increases the ability of the cells expressing the 5-HT$_{2C}$-R gene to respond to a stimulation by serotonin.

In this other aspect, a particular subject of the present invention is also a compound capable of increasing the editing rate of an editing site of an RNA fragment comprising the sequence SEQ ID No. 33 (5'-AUA CGU AAU CCU A-3') of the 5-HT$_{2C}$-R mRNA, which editing site when it is edited, modifies the sequence of the amino acids of the second intracellular loop of 5-HT$_{2C}$-R, for the treatment of mania or of certain forms of schizophrenia, in particular if this increase in editing rate decreases the ability of the cells expressing the 5-HT$_{2C}$-R gene to respond to a stimulation by serotonin.

The following examples and also the figures and the legends hereinafter have been chosen to provide those skilled in the art with a complete description in order to be able to implement and use the present invention. These examples are not intended to limit the scope of what the inventor considers to be its invention, nor are they intended to show that only the experiments hereinafter were carried out.

FIGURE LEGENDS

FIGS. 1A to 1O: Examples of analytical profiles for 5-HT$_{2C}$ receptor editing, obtained by means of the SSCP method described above. Under the conditions of this example (amplification of a 250 base pair fragment and analysis by capillary electrophoresis), the editing profiles obtained using RNA from rat choroids plexus (FIG. 1A) and from rat total brain (FIG. 1B) are characteristic of each of these structures. The relative importance of each of the mutations can be determined from the standard editing profiles for each of the separate editing forms which are characteristic of each form corresponding to a given mutant combination of the 5-HT$_{2C}$receptor on one or more of the 5 editing sites (A, B, C, D and C') amplified and analyzed under the same conditions (FIGS. 1C to 1O). The editing profiles of all the separate editing forms were obtained, but are not all represented here.

EXAMPLE 1

Method for Determining, by Specific Hybridization and in a Single Step, the Percentage of Each of the Thirty-two Forms of the 5-HT$_{2C}$-R mRNA The method described hereinafter makes it possible to determine, by specific hybridization and in a single step, the percentage of each of the thirty-two forms of the 5-HT$_{2C}$-R mRNA even if amplification of the information contained in these mRNAs was necessary.

After mRNA editing, the As are replaced with Is which, in turn, are replaced with dGs in the cDNA. In other words, the greater the number of As converted to Is during the initial mRNA editing, the higher the temperature required for specific hybridization. The replacement of the dGs with dis makes it possible to perform the hybridizations at a single temperature according to the strategy described below.

If necessary, if the amount of starting mRNA is too small, the information amplified in vitro can be done so in the form of single-stranded RNA, in a linear manner by in vitro transcription (IVT); it can also be done so in the form of double-stranded DNA by RT-PCR, after reverse transcription (RT) of the mRNA followed by exponential amplification by PCR. Whether the information is amplified in the final form of a single-stranded RNA or in that of a double-stranded DNA, there is the problem of identifying the Is since, in all cases, during the synthesis of the cDNA by means of reverse transcriptase, a dC is incorporated opposite each I and, during the synthesis of the complementary strand, a dG is then incorporated opposite each dC. This amounts to saying that if the sequences which are hybridized to the various probes are those which are complementary to the initial mRNAs, they contain dTs or Us opposite each unedited A, and dCs or Cs opposite each 1, according to whether the sequences were obtained in the form of DNA by RT-PCR or in the form of RNA by IVT.

When the information contained in the starting mRNAs is amplified by IVT of the sense strand, the RNA molecules synthesized have a sequence identical to that of the mRNAs, but in which the As, edited to Is, are replaced with Gs. Conversely, the IVT of the antisense strand makes it possible to synthesize RNA molecules in which the sequence is complementary to that of the starting mRNAs, but with Cs, which replace the Us opposite the sites edited from A to I.

Consequently, in order for the hybridization temperatures to be identical for all the probes, the single-stranded DNAs deposited in the form of probes on the support have a sequence identical to those of the initial mRNAs, but in which dAs replace the unedited As, and dIs replace Is originating from the editing of these As to Is. Thus, whether the initial RNAs were amplified by RT-PCR in the form of double-stranded DNA or by IVr in the form of antisense RNA from the initial mRNAs, there will always be the formation of two hydrogen bonds between dA and dT or U, on the one hand, and between dI and dC or C, on the other hand.

The sequences of the thirty-two probes required for identifying the various edited or unedited forms of the 5-HT$_{2C}$-R mRNA are reported below.

The Tm values having been measured individually for each of the probes, all the conditions other than the temperature being identical moreover, the hybridization temperature for all the probes is chosen between the two extreme Tm values measured; in this case, for the probe of sequence SEQ ID No. 1 and the probe of sequence SEQ ID No. 32.

The conditions other than the Tm will have been defined such that the difference between the two extreme Tm values measured is as small as possible.

The various initial forms of the 5-HT$_{2C}$-R mRNA are quantified by measuring either the radioactivity or the fluorescence intensity of the thirty-two sequences paired. Since the sum of the thirty-two values measured is directly proportional to the sum of the various initial forms of the 5-HT$_{2C}$-R mRNA, the percentage of each of the forms of this mRNA can be deduced by dividing the value measured individually for each form by the sum of the values of the thirty-two forms.

| | Editing sites | A B EC D | | |
|---|---|---|---|---|
| 1 | 5-HT$_{2C}$R-0<br>I-N-I | d(CAATACGTAATCCTATT) | SEQ ID No. 1 |
| 2 | 5-HT$_{2C}$R-A<br>V-N-I | d(CAITACGTAATCCTATT) | SEQ ID No. 2 |
| 3 | 5-HT$_{2C}$R-B<br>M-N-I | d(CAATICGTAATCCTATT) | SEQ ID No. 3 |
| 4 | 5-HT$_{2C}$R-C<br>I-S-I | d(CAATACGTAITCCTATT) | SEQ ID No. 4 |
| 5 | 5-HT$_{2C}$R-D<br>I-N-V | d(CAATACGTAATCCTITT) | SEQ ID No. 5 |
| 6 | 5-HT$_{2C}$R-E<br>I-D-I | d(CAATACGTIATCCTATT) | SEQ ID No. 6 |
| 7 | 5-HT$_{2C}$R-AB<br>V-N-I | d(CAITICGTAATCCTATT) | SEQ ID No. 7 |
| 8 | 5-HT$_{2C}$R-AC<br>V-S-I | d(CAITACGTAITCCTATT) | SEQ ID No. 8 |
| 9 | 5-HT$_{2C}$R-AD<br>V-N-V | d(CAITACGTAATCCTITT) | SEQ ID No. 9 |
| 10 | 5-HT$_{2C}$R-AE<br>V-D-I | d(CAITACGTIATCCTATT) | SEQ ID No. 10 |
| 11 | 5-HT$_{2C}$R-BC<br>M-S-I | d(CAATICGTAITCCTATT) | SEQ ID No. 11 |
| 12 | 5-HT$_{2C}$R-BD<br>M-N-V | d(CAATICGTAATCCTITT) | SEQ ID No. 12 |
| 13 | 5-HT$_{2C}$R-BE<br>M-D-I | d(CAATICGTIATCCTATT) | SEQ ID No. 13 |
| 14 | 5-HT$_{2C}$R-CD<br>I-S-V | d(CAATACGTAITCCTITT) | SEQ ID No. 14 |
| 15 | 5-HT$_{2C}$R-CE<br>I-G-I | d(CAATACGTIITCCTATT) | SEQ ID No. 15 |
| 16 | 5-HT$_{2C}$R-DE<br>I-D-V | d(CAATACGTIATCCTITT) | SEQ ID No. 16 |
| 17 | 5-HT$_{2C}$R-ABC<br>V-S-I | d(CAITICGTAITCCTATT) | SEQ ID No. 17 |
| 18 | 5-HT$_{2C}$R-ABD<br>V-N-V | d(CAITICGTAATCCTITT) | SEQ ID No. 18 |
| 19 | 5-HT$_{2C}$R-ABE<br>V-D-I | d(CAITICGTIATCCTATT) | SEQ ID No. 19 |
| 20 | 5-HT$_{2C}$R-ACD<br>V-S-V | d(CAITACGTAITCCTITT) | SEQ ID No. 20 |
| 21 | 5-HT$_{2C}$R-ACE<br>V-G-I | d(CAITACGTIITCCTATT) | SEQ ID No. 21 |
| 22 | 5-HT$_{2C}$R-ADE<br>V-D-V | d(CAITACGTIATCCTITT) | SEQ ID No. 22 |
| 23 | 5-HT$_{2C}$R-BCD<br>M-S-V | d(CAATICGTAITCCTITT) | SEQ ID No. 23 |
| 24 | 5-HT$_{2C}$R-BCE<br>M-G-I | d(CAATICGTIITCCTATT) | SEQ ID No. 24 |
| 25 | 5-HT$_{2C}$R-BDE<br>M-D-V | d(CAATICGTIATCCTITT) | SEQ ID No. 25 |
| 26 | 5-HT$_{2C}$R-CDE<br>I-G-V | d(CAATACGTIITCCTITT) | SEQ ID No. 26 |
| 27 | 5-HT$_{2C}$R-ABCD<br>V-S-V | d(CAITICGTAITCCTITT) | SEQ ID No. 27 |
| 28 | 5-HT$_{2C}$R-ABCE<br>V-G-I | d(CAITICGTIITCCTATT) | SEQ ID No. 28 |
| 29 | 5-HT$_{2C}$R-ABDE<br>V-D-V | d(CAITICGTIATCCTITT) | SEQ ID No. 29 |
| 30 | 5-HT$_{2C}$R-ACDE<br>V-G-V | d(CAITACGTIITCCTITT) | SEQ ID No. 30 |
| 31 | 5-HT$_{2C}$R-BCDE<br>M-G-V | d(CAATICGTIITCCTITT) | SEQ ID No. 31 |
| 32 | 5-HT$_{2C}$R-ABCDE<br>V-G-V | d(CAITICGTIITCCTITT) | SEQ ID No. 32 |

The Tm values having been measured individually for each of the probes, all the conditions other than the temperature being identical moreover, the inventors thus demonstrated that it was possible to very significantly reduce the difference obtained between the two extreme Tm values measured ($\Delta Tm_{ext}$) for the probe of sequence SEQ ID No. 1 and the probe of sequence SEQ ID No. 32, compared with the difference obtained between the two extreme Tm values measured for the normal probes (array of probes of the invention in which the dIs are replaced with dGs).

Results for the array of probes of sequences SEQ ID Nos. 1 to 32 of the invention:

$\Delta Tm_{ext}$ (in ° C.)=61.1±0.13−54.13+0.44, i.e. approximately 6.97° C.;

for the array of normal probes (without dIs):

$\Delta Tm_{ext}$ (in ° C.)=74.1±0.2−61.1±0.13, i.e. approximately 13.00° C.

Specificity of the Array of Probes of the Invention

The inventors also demonstrated that, at the hybridization temperature which will be chosen for all the probes of the invention (between 61.1 and 54.13° C., preferably in the region of the mean value of 57.6° C.), the probe SEQ ID No. 32 of the invention does not hybridize with an oligonucleotide complementary to this probe, with the exception of the base located in the position complementary to the dI located at position 15 of the probe SEQ ID No. 32 (Tm of 49.4° C.).

EXAMPLE 2

Example of Implementation

The example of implementation developed below concerns the mRNA editing with, for application, editing of the mRNAs of one of the serotonin receptors. This example shows that it is possible to perform a hybridization under single temperature conditions, even when the percentage of guanines and cytosines initially paired goes from less than 30% to close to 60%, in a short sequence.

Five adenosines can be potentially edited in three different codons, which gives $2^5=32$ different combinations of mRNA sequences and 3×4×2=24 different combinations of amino acid sequences (see scheme below). The deamination of the adenosines at the five sites that can be edited, given the notations A to E (or alternatively A, B, C, D and C'), results in the replacement of three amino acids of the second intracellular loop of 5-HT$_{2C}$-R. The 5-HT$_{2C}$-R synthesized by translation of the unedited mRNA (SEQ ID No. 34) consists of the amino acids I-N-I (isoleucine-asparagine-isoleucine) in the second intracellular loop, whereas that synthesized by translation of the completely edited mRNA (SEQ ID No. 35) or mRNA edited simultaneously at the A, E, C and D sites consists of the amino acids V-G-V (valine-glycine-valine), the codons IUI or IUA both specifying the incorporation of a valine, if I is effectively read as G. Since the codons AUI, AIU and IAU specify respectively the incorporation of M (methionine), S (serine) and D (aspartic acid), twenty-four combinations of amino acids are effectively possible in the second intracellular loop of 5-HT$_{2C}$-R, for thirty-two combinations of different sequences of its mRNA.

| A B | EC | D | Editing sites |
|---|---|---|---|
| 5'-CA AUA CGU AAU CCU AUU-3' | | | unedited 5-HT$_{2C}$-R mRNA5-HT$_{2C}$-R (SEQ. ID NO: 34) |
| I R N P I | | | amino acids (unedited mRNA) (SEQ. ID NO: 38) |
| 5'-CA IUI CGU IIU CCU IUU-3' | | | completely edited 5-HT$_{2C}$-R mRNA (SEQ ID NO: 35) |
| V G V | | | 5-HT$_{2C}$-R amino acids (completely edited mRNA) |
| IUA | | | Editing of the A site |
| V | | | 5-HT$_{2C}$-R amino acids (mRNA edited at the A site) |
| AUI | AIU | | Editing of the B and C sites |
| M | S | | 5-HT$_{2C}$-R amino acids (mRNA edited at the B and C sites) |
| | IAU | | Editing of the E site |
| | D | | 5-HT$_{2C}$-R amino acid (mRNA edited at the E site) |

The second intracellular loop of 5-HT$_{2C}$-R is involved in the coupling of the receptor to trimeric Gq proteins. A 5-HT$_{2C}$-R (I-N-I) synthesized by translation of the unedited mRNA exhibits constitutive coupling activity and therefore permanent activation of phospholipase Cβ, whereas a 5-HT$_{2C}$-R (V-G-V) synthesized by translation of a completely edited mRNA responds less well to stimulation by serotonin due to a lack of coupling to trimeric Gq proteins. In other words, according to its degree of editing, 5-HT$_{2C}$-R will exhibit a greater or lesser ability to respond to stimulation by serotonin.

Being able to measure the percentage represented by each of the thirty-two possible forms of mRNA amounts to predicting the percentage of each of the twenty-four forms of 5-HT$_{2C}$-R and, consequently, to being able to indirectly estimate the effectiveness of 5-HT$_{2C}$-R response to stimulation by serotonin. Two methods were used to estimate the percentages of the various forms of 5-HT$_{2C}$-R mRNA. These two methods do not give equivalent information.

The first method, which is technically the most laborious and the most expensive, makes it possible to statistically estimate the percentage of each of the thirty-two forms of the 5-HT$_{2C}$-R mRNA. It consists in simultaneously synthesizing all the cDNAs of the 5-HT$_{2C}$-R mRNAs by means of specific primers common to the various mRNA forms, and then in inserting all these cDNAs into plasmids which are then transfected into bacteria. After transformation and selection, these bacteria are then cloned. These cloned bacteria are then amplified and the plasmid DNA is then extracted therefrom and purified and the inserted cDNAs are then sequenced. If the number of cDNAs cloned and sequenced is sufficient to be statistically representative of the initial population of cDNA, and therefore of mRNA, the percentage of each of the initial forms of 5-HT$_{2C}$-R mRNA may then be deduced. If this number is insufficient, only the major forms of the 5-HT$_{2C}$-R mRNA will be statistically represented.

The second method can be carried out more rapidly but it does not make it possible to estimate the percentage of each of the thirty-two forms of the 5-HT$_{2C}$-R mRNA. On the other hand, it makes it possible to determine the percentage of each A edited to 1, at each of the five sites that can be edited. For this, after synthesis of the cDNAs as in the preceding case, a primer extension is carried out in the presence of three of the four usual deoxyribonucleoside triphosphates and of a dideoxyribonucleoside triphosphate which terminates the primer extension opposite the deoxyribonucleoside whose nature it is desired to determine. For example, the three deoxyribonucleoside triphosphates may be dATP, dGTP and dTTP, while the dideoxyribonucleoside triphosphate is ddCTP (dideoxycytidine triphosphate) which, by incorporating itself opposite the first dG encountered, stops the primer extension at the position where there was an I in the mRNA which served as a matrix for the cDNA synthesis. When the initial adenosine has not been edited and therefore replaced with a dG in the cDNA, the primer is extended until the first dG which follows the dA originating from the unedited adenosine. Under these conditions, the primers must be judiciously chosen, complementary to one or other of the two strands of the cDNA, and must also have been labeled with $^{32}$P in the 5' position, in order to be visualized by autoradiography after separation by polyacrylamide gel electrophoresis. Measurement of the radioactivity contained in the various separated fragments makes it possible to estimate the percentage of As edited at each of the five sites that can be edited. At least as many primers as there are sites that can be edited are necessary.

EXAMPLE 3

Identification and Quantification of the Various (Edited or Unedited) Forms and Determination of the mRNA Editing Profile by SSCP (Single Strand Conformation Polymorphism) of the Complementary DNAs I) Protocol 1—Total RNA Extraction:

To extract the RNAs from frozen tissues in the RNA Later solution (appendix C), or freshly dissected tissues, these tissues are ground in 350 µl of the RA1 solution of the NucleoSpin RNA II extraction kit (appendix B1), to which 3.5 µl of β-mercaptoethanol have been added (appendix C). The lysate is filtered by centrifugation on a filtration column (appendix B1) at 11000×g for 1 minute. After homogenization of the filtrate with 350 µl of a 700 ethanol solution, the entire mixture is centrifuged on a Nucleospin RNAII silica column (appendix B1) for 30 seconds at 8000×g. The column is then washed using 350 µl of the MDB (membrane desalting buffer) solution (appendix B1) and centrifugation for 30 seconds at 11000×g. In order to remove any possible contaminating genomic DNA, 10 µl of the DNase I solution (appendix B1) are placed on the column for 30 minutes at ambient temperature. After complete digestion of the DNA, the DNase I is removed by washing with 200 µl of the RA2 solution (appendix B1) and then further washing with 600 µl of the RA3 solution (appendix B1), each wash being followed by centrifugation for 30 seconds at 8000 g. The RNA attached to the column is washed a final time with 250 µl of the RA3 solution (appendix B1) and finally dried by centrifugation for 2 minutes at 11000 g. The RNA is eluted with 60 µl of RNAse-free water (appendix B1), after centrifugation for 1 minute at 11000 g.

2—Reverse Transcription:

For this step, the ThermoScript RT-PCR system kit and protocol (appendix B2) are used. For each RNA sample, 500 ng of total RNA are mixed with 1 µl of poly-(dT)20 (50 µM; appendix B2), optionally made up to a final volume of 10 µl with RNase-free water (appendix B2). This volume is incubated for 5 minutes at 65° C. and is then immediately cooled in ice. 4 µl of the cDNA synthesis buffer (5×concentrated; appendix B2), 1 µl of the DTT solution (DTT for dithiothreitol) (0.1 M; appendix B2), 1 µl of RNase OUT (40 U/gl; appendix B2), 1 µl of RNase-free water (appendix B2), 2 µl of a mixture of dNTP (dNTP: deoxyribonucleotide triphosphate) (10 mM each; appendix B2) and 1 µl of the thermoScript RT enzyme (15 U/µl; appendix B2) are then added, and the entire mixture is incubated at 50° C. for 60 minutes. The reaction is then stopped by heating the reaction mixture at 85° C. for 5 minutes. To remove the RNA, the reaction medium is incubated in the presence of 1 µl of RNase H (appendix B2) at 37° C. for 20 minutes.

3—PCR Amplification:

The example here is given specifically for the 5-HT$_{2C}$-R gene. Those skilled in the art may readily transpose or adapt such a PCR amplification protocol to other mRNAs which may be edited by choosing the pair of primers for specifically amplifying the mRNA fragment comprising the editing sites.

The pair of primers PCR9, PCR10, used for the PCR amplification of a fragment of the 5-HT$_{2C}$-R gene, was chosen in DNA regions that are identical in humans, mice and rats. The sequences of the pair of primers are:

```
PCR9    TGTCCCTAGCCATTGCTGATATGCT;    (SEQ ID No. 36)
and

PCR10   GCAATCTTCATGATGGCCTTAGTCCG.   (SEQ ID No. 37)
```

The resulting PCR amplification product is 250 base pairs in size, in the 3 species human, mouse and rat.

For the demonstration of SSCP (single strand conformation polymorphism), these primers can be labeled with various fluorophores such as C6-FAM or HEX.

For the PCR amplification step (PCR for "Polymerase Chain Reaction"), the Platinum Taq DNA polymerase protocol and kit (appendix B3) are used. For the PCR amplification of a region that includes the 5-HT$_{2C}$-R gene editing site, the reaction mixture comprises 2 µl of the cDNA solution, 5 µl of the amplification buffer (10 times concentrated; appendix B3), 1.5 µl of an MgCl$_2$ solution (50 mM; appendix B3), 1 µl of a mixture of the four dNTPs (10 mM each; appendix B3), 1 µl of each of the primers PCR9 and PCR10 (solution at 10

μM), 0.5 μl of the Platinum Taq enzyme (5 units per ml; appendix B3), made up to 50 μl with sterile distilled water. This reaction volume is initially heated in a PTC200 thermocycler (appendix A) for 2 minutes at 94° C. It is then subjected to 30 cycles comprising phases of denaturation at 94° C. for 30 seconds, and then of hybridization for 30 seconds at 65° C. decreased by 0.3° C. for each subsequent cycle, and of elongation at 72° C. for 30 seconds. A final elongation step is carried out at 72° C. for 6 minutes.

4—Purification of PCR Products:

For this purification step, the Nucleospin Extract protocol and kit (appendix B4) are used. The reaction volume obtained by PCR (50 μl) is mixed with 200 μl of the NT2 solution (appendix B4) and directly loaded onto the purification column. After centrifugation at 11000 g for 1 minute, the PCR amplification products attached to the column are washed using 600 μl of the NT3 solution (appendix B4) and centrifugation at 11000 g for 1 minute. A final wash is carried out with 200 μl of the NT3 solution (appendix B4) and the column is then dried by centrifugation at 11000 g for 2 minutes. Elution of the DNA is obtained by incubating the column with 50 μl of the NE elution buffer (appendix B4) at ambient temperature for 1 minute, followed by centrifugation at 11000 g for 1 minute.

5—Quantification of the PCR Products using the Agilent 2100 Bioanalyzer:

The DNA 1000 Assay kit and protocol (appendix B5) and the 2100 bioanalyzer (appendix A) are used to determine the concentration of DNA obtained after PCR amplification and column purification. The gel is prepared by vigorously mixing an aliquot of gel (appendix B5) with 25 μl of dye (appendix B5). This matrix is then centrifuged at 2400 g for 15 minutes and is then injected (9 μl) into the microcapillaries of the DNA chip (appendix B5). For the quantification, the PCR DNA samples (1 μl) are loaded into the corresponding wells, in the presence of an internal size indicator (5 μl; appendix B5) and of another size marker (1 μl; appendix B5). The electrophoresis and the calculation of the concentration of DNA are carried out by running the BioSizing program of the 2100 Bioanalyzer (appendix A).

6—Separation of the Single Stranded DNA by Capillary Electrophoresis:

The analysis of the PCR-amplified DNA labeled on each of the 2 strands with fluorophores of C6-FAM and HEX type (appendix C) is carried out by capillary electrophoresis on the ABI PRISM 3100 device (appendix A). The DNA samples to be analyzed are first of all diluted in water to a concentration of 250 pg/μl. For each sample, a mixture is prepared that contains 1 μl of the purified and diluted PCR product solution, 0.5 μl of GeneScan 500 ROX migration standard, 0.5 μl of an NaOH solution (0.3 N) and 10.5 μl of formamide. This mixture is brought to 90° C. for 2 minutes and is then immediately cooled in ice. The capillary electrophoresis begins with a premigration of 3 minutes at 15000 volts. The DNA is injected at 1000 volts, for a period of 22 seconds. Finally, the electrophoresis of the DNA is carried out at 15000 volts and 18° C. in a one-times concentrated TBE buffer (TBE for Tris-Borate-EDTA) containing the GeneScanPolymer gel (5%) and glycerol (10%). At this stage, the fluorescence reading and the data acquisition are carried out automatically. These data are visualized and processed using the GeneScan analysis program.

The results make it possible in particular to obtain an editing profile of said mRNA under given conditions (length of the PCR products, conditions of the above steps of the SSCP protocol, parameters for the data processing, etc). The parameters of this profile (such as the migration time, the height and the surface area of the peaks observed on this profile) will be or may be compared to standard profiles, for instance:

to the characteristic profile obtained under these given conditions for each of the separate edited (or unedited) forms of said mRNA (cf. for example FIGS. 1C to 1O showing the characteristic profiles obtained for 13 of the 32 edited or unedited forms of the 5-HT$_{2C}$-R mRNA, this characteristic profile having been obtained for the 32 potential forms SEQ ID Nos. 1 to 32); and/or to profiles corresponding to known qualitative and/or quantitative mixtures of each of these edited or unedited forms, obtained under given conditions; and/or to known editing profiles of the same mRNA for normal patients or patients presenting confirmed pathologies, for mRNA extracts of specific tissues (cf. for example FIGS. 1A and 1B) under these same given conditions, all these profiles being or possibly being stored in the memory of the analysis program. Those skilled in the art of signal analysis and processing will readily be able to demonstrate, on such an editing profile, the similarities and/or the differences with the standardized editing profiles stored and annotated in the memory (percentages and rate of editing, pathology induced, appropriate therapeutic treatment, etc.).

For each of these "standard" profiles stored in the memory of the analysis program and obtained under these given conditions, the percentage and/or the rate of editing for each of the forms may also be known.

To obtain the characteristic profile of each of the edited (or unedited) forms of said mRNA by SSCP under given conditions (steps 1 to 6 in Example 3), the following process may be carried out:

cloning and verification by sequencing of the edited or unedited form for which it is desired to obtain the characteristic profile;

PCR amplification of the identified and cloned sequence (step 3 of Example 3);

implementation of steps 4 to 6 of Example 3.

In order to determine the editing percentages and/or the editing rate for standard profiles corresponding to known mixtures of edited or unedited forms, it is sufficient to mix, before step 3 of the above process, in the desired proportions, the editing forms included in the mixture.

To determine the editing percentages and/or rate for standard profiles corresponding to reference editing profiles which may be in the memory of the analysis system, it being possible for these profiles in particular to correspond to editing profiles obtained for normal patients or patients exhibiting a confirmed pathology, for a particular tissue, before or after therapeutic treatment, etc., it will be sufficient to clone and sequence a representative portion of or all the sequences of said mRNA present in the mRNA extract and to deduce therefrom the proportion of each of the forms present.

In another method, it will also be possible to use the biochips of the invention on which all the editing forms of said mRNA will be deposited.

II) Appendices

A—List of Materials:

ABI Prism 3100 (Applied Biosystems);

2100 Bioanalyzer (Agilent Technologies; No. DE13701290);

Eppendorf Centrifuge 5415 D (serial No. 5425 39 178); and

MJ Research PTC200 Thermocycler (serial No. AL046013 and EN015975).

B—List of Kits:
1—NucleoSpin RNA II (Invitrogen; reference: 740.955.50);
2—ThermoScript RT-PCR system (Invitrogen; reference: 11146-024);
3—Platinum Taq DNA polymerase (Invitrogen; reference: 10966-026);
4—Nucleospin Extract (Macherey-Nagel; reference: 740.588.50); and
5—DNA 1000 Assay (Agilent Technologies; reference: 5065-4449).

C—List of Solutions:
β-mercaptoethanol (Sigma; reference: M 3148);
primer PCR 9 (Proligo; 5'-labeled with the fluorophore C6-FAM and purified);
primer PCR 10 (Proligo; 5'-labeled with the fluorophore HEX and purified); and
10×TBE (Invitrogen; reference: 15581-044).

EXAMPLE 4

Selection of a Compound Capable of Modulating the Editing Rate of the Fragment Comprising the Sequence SEQ ID No. 33 (5'-AUA CGU MU CCU A-3') of the 5-$HT_{2C}$-R mRNA in the Mouse 1) Bringing said compound to be evaluated into contact with a population of eukaryotic cells, in particular murine cells, expressing the gene of said mRNA (in vitro, in cellulo or in vivo)

Example (In Vivo)

Intraperitoneal injection of Balb C mice with the compound to be tested, approximately 20 mg/Kg.
At given times, for example up to 3 days: the mice are killed and a sample of specific tissue, such as the prefrontal cortex, is removed, frozen and then microdissected.

2) Demonstration of the modulation of the editing of said mRNA fragment in the cells using an mRNA extract, by means of the pair of primers PCR9 (SEQ ID No. 36) and PCR10 (SEQ ID No. 37).

cf. Example 3.

3) Comparison of the editing rate and/or of the editing profile obtained with that obtained for an mRNA extract derived from the same population of cells from control mice that have not been brought into contact with the compound to be evaluated, and demonstration of the modulation or non-modulation of the editing rate and/or profile.

Where appropriate,

4) Comparison of the editing rate and/or of the editing profile obtained with the standard profiles obtained under the same analytical conditions for identical cell populations after treatment with a compound known to modulate the editing rate and/or profile of said mRNA, and the therapeutic effect of which is known, and selection of said compound tested as a potential agent for exerting the same therapeutic effect if the modulation observed for the product tested is similar to that observed for the known compound.

EXAMPLE 5

Compound Capable of Modulating the Editing Rate of the Fragment Comprising the Sequence SEQ ID No. 33 (5'-AUA CGU MU CCU A-3') of the 5-$HT_{2C}$-R mRNA, Exhibiting Therapeutic Activity It was possible to demonstrate that a compound known to be an active antidepressant was capable of modulating the 5-$HT_{2C}$-R editing rate.

---

The invention claimed is:

1. A Single Strand DNA Conformation Polymorphism (SSCP) method for obtaining the editing profile of 5-HT2c-r mRNA, using a specific tissue sample or using a sample of a population of eukaryotic cells, characterized in that the method comprises:
   a) extraction of the total RNA of said sample, followed, where appropriate, by purification of the mRNA;
   b) reverse transcription of the RNA extracted in step a) and synthesis of the double-stranded DNA;
   c) PCR amplification of the DNA obtained in step b) using the following pair of primers specific for 5-HT2c-r mRNA, wherein said mRNA may be edited; PCR9 TGTCCCTAGCCATTGCTGATATGCT (SEQ ID No. 36); and PCR 10 GCAATCTTCATGATGGCCTTAGTCCG (SEQ ID No. 37);
   d) where appropriate, purification of the PCR products obtained in step c);
   e) where appropriate, quantification of the PCR products obtained in step d);
   f) dissociation of the double-stranded DNA to single-stranded DNA, in particular by heating followed by abrupt cooling;
   g) separation of the single-stranded DNA by capillary electrophoresis;
   h) obtaining of the editing profile by reading fluorescence and, where appropriate, acquisition of profile data by means of an exploitation system associated with a fluorescence reader and
   i) showing at least 13 characteristics profile of the edited or unedited forms of the 5-HT2c-r mRNA.

2. The SSCP method as claimed in claim 1, characterized in that the pair of primers is labeled with fluorophores.

3. An SSCP method for obtaining the editing profile and the editing rate of an mRNA, wherein said mRNA may be edited, using a specific tissue sample or using a sample of a population of eukaryotic cells, characterized in that the method comprises:
   a) obtaining an editing profile of 5-HT2c-r mRNA by the SSCP method as claimed in one of claims 1 or 2;
   b) comparing the profile obtained in step a) with standard profiles corresponding to:
   characteristic profiles obtained, for each of the edited (or unedited) separate forms of said mRNA; and/or
   characteristic profiles of known qualitative and/or quantitative mixtures of each of these edited or unedited forms, and/or
   known editing profiles, of this same mRNA for normal patients or patients presenting confirmed pathologies, for mRNA extracts of said specific tissues, or else for said population of eukaryotic cells;
   c) selecting the known editing profile corresponding to the editing profile obtained in step a); and
   d) associating the editing rate of the profile selected in step c) with the editing profile obtained in step a).

* * * * *

UNITED STATES PATENT AND TRADEMARK OFFICE
CERTIFICATE OF CORRECTION

PATENT NO. : 7,635,558 B2 Page 1 of 1
APPLICATION NO. : 10/522592
DATED : December 22, 2009
INVENTOR(S) : Jean-Jacques Madjar et al.

It is certified that error appears in the above-identified patent and that said Letters Patent is hereby corrected as shown below:

Title Page Abstract; Item 57, line 2, "deoxyinostines" should read --deoxyinosines--.

Title Page Abstract; Item 57, line 2, "deoxyguanogines" should read --deoxyguanosines--.

Signed and Sealed this

Ninth Day of February, 2010

David J. Kappos
*Director of the United States Patent and Trademark Office*

SEQUENCE LISTING

<160> NUMBER OF SEQ ID NOS: 38

<210> SEQ ID NO 1
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide

<400> SEQUENCE: 1
caatacgtaa tcctatt                                                      17

<210> SEQ ID NO 2
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine

<400> SEQUENCE: 2
cantacgtaa tcctatt                                                      17

<210> SEQ ID NO 3
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine

<400> SEQUENCE: 3
caatncgtaa tcctatt                                                  17

<210> SEQ ID NO 4
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (10)
<223> OTHER INFORMATION: inosine

<400> SEQUENCE: 4
caatacgtan tcctatt                                                  17

<210> SEQ ID NO 5
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (15)
<223> OTHER INFORMATION: inosine

<400> SEQUENCE: 5
caatacgtaa tcctntt                                                  17

<210> SEQ ID NO 6
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (9)
<223> OTHER INFORMATION: inosine

<400> SEQUENCE: 6
caatacgtna tcctatt                                                  17

<210> SEQ ID NO 7
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)

```
<223> OTHER INFORMATION: inosine
<220> FEATURE:
<221> NAME/KEY: modified_base
<222> LOCATION: (5)
<223> OTHER INFORMATION: inosine

<400> SEQUENCE: 7
cantncgtaa tcctatt                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (10)
<223> OTHER INFORMATION: inosine

<400> SEQUENCE: 8
cantacgtan tcctatt                                                    17

<210> SEQ ID NO 9
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (15)
<223> OTHER INFORMATION: inosine

<400> SEQUENCE: 9
cantacgtaa tcctntt                                                    17

<210> SEQ ID NO 10
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine

<400> SEQUENCE: 10
cantacgtna tcctatt                                                    17

<210> SEQ ID NO 11
<211> LENGTH: 17
<212> TYPE: DNA
<213> ORGANISM: Artificial Sequence
<220> FEATURE:
```

```
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (10)
<223> OTHER INFORMATION: inosine

<400> SEQUENCE: 11
caatncgtan tcctatt                                                    17

<210> SEQ ID NO 12
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (15)
<223> OTHER INFORMATION: inosine

<400> SEQUENCE: 12
caatncgtaa tcctntt                                                    17

<210> SEQ ID NO 13
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine

<400> SEQUENCE: 13
caatncgtna tcctatt                                                    17

<210> SEQ ID NO 14
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 14
caatacgtan tcctntt                                                    17
```

```
<210> SEQ ID NO 15
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine

<400> SEQUENCE: 15
caatacgtnn tcctatt                                                  17

<210> SEQ ID NO 16
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (15)
<223> OTHER INFORMATION: inosine

<400> SEQUENCE: 16
caatacgtna tcctntt                                                  17

<210> SEQ ID NO 17
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (10)
<223> OTHER INFORMATION: inosine

<400> SEQUENCE: 17
cantncgtan tcctatt                                                  17

<210> SEQ ID NO 18
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
```

```
<221> NAME/KEY: modified_base
<222> LOCATION: (5)
<223> OTHER INFORMATION: inosine
<220> FEATURE:
<221> NAME/KEY: modified_base
<222> LOCATION: (15)
<223> OTHER INFORMATION: inosine

<400> SEQUENCE: 18
cantncgtaa tcctntt                                                              17

<210> SEQ ID NO 19
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine

<400> SEQUENCE: 19
cantncgtna tcctatt                                                              17

<210> SEQ ID NO 20
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 20
cantacgtan tcctntt                                                              17

<210> SEQ ID NO 21
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine
<220> FEATURE:
```

```
<221> NAME/KEY: modified_base
<222> LOCATION: (10)
<223> OTHER INFORMATION: inosine

<400> SEQUENCE: 21
cantacgtnn tcctatt                                                    17

<210> SEQ ID NO 22
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (15)
<223> OTHER INFORMATION: inosine

<400> SEQUENCE: 22
cantacgtna tcctntt                                                    17

<210> SEQ ID NO 23
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 23
caatncgtan tcctntt                                                    17

<210> SEQ ID NO 24
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine
```

```
<400> SEQUENCE: 24
caatncgtnn tcctatt                                                        17

<210> SEQ ID NO 25
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (15)
<223> OTHER INFORMATION: inosine

<400> SEQUENCE: 25
caatncgtna tcctntt                                                        17

<210> SEQ ID NO 26
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 26
caatacgtnn tcctntt                                                        17

<210> SEQ ID NO 27
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine
```

```
<400> SEQUENCE: 27
cantncgtan tcctntt                                                        17

<210> SEQ ID NO 28
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine

<400> SEQUENCE: 28
cantncgtnn tcctatt                                                        17

<210> SEQ ID NO 29
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (15)
<223> OTHER INFORMATION: inosine

<400> SEQUENCE: 29
cantncgtna tcctntt                                                        17

<210> SEQ ID NO 30
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine
<220> FEATURE:
```

-continued

```
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 30
cantacgtnn tcctntt                                                          17

<210> SEQ ID NO 31
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 31
caatncgtnn tcctntt                                                          17

<210> SEQ ID NO 32
<211> LENGTH: 17
<212> TYPE: DNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 32
cantncgtnn tcctntt                                                          17

<210> SEQ ID NO 33
<211> LENGTH: 13
<212> TYPE: RNA
<213> ORGANISM: Artificial Sequence
```

```
<220> FEATURE:
<223> OTHER INFORMATION: Description of the Artificial Sequence:
      Synthetic oligonucleotide

<400> SEQUENCE: 33
auacguaauc cua                                                              13

<210> SEQ ID NO 34
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(17)

<400> SEQUENCE: 34 ca aua cgu aau ccu auu                                                      17
   Ile Arg Asn Pro Ile
    1               5

<210> SEQ ID NO 35
<211> LENGTH: 17
<212> TYPE: RNA
<213> ORGANISM: Artificial Sequence
<220> FEATURE:
<223> OTHER INFORMATION: Description of the Artificial Sequence:
      Synthetic oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (5)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (15)
<223> OTHER INFORMATION: inosine

<400> SEQUENCE: 35
canuncgunn uccunuu                                                          17

<210> SEQ ID NO 36
<211> LENGTH: 25
<212> TYPE: DNA
<213> ORGANISM: Artificial Sequence
<220> FEATURE:
<223> OTHER INFORMATION: Description of the Artificial Sequence:
      Synthetic primer

<400> SEQUENCE: 36
tgtccctagc cattgctgat atgct                                                 25

<210> SEQ ID NO 37
<211> LENGTH: 26
<212> TYPE: DNA
<213> ORGANISM: Artificial Sequence
<220> FEATURE:
```

```
<223> OTHER INFORMATION: Description of the Artificial Sequence:
      Synthetic primer

<400> SEQUENCE: 37
gcaatcttca tgatggcctt agtccg                                          26

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Arg Asn Pro Ile
1               5
```